US009271962B2

(12) United States Patent
Makriyannis et al.

(10) Patent No.: US 9,271,962 B2
(45) Date of Patent: Mar. 1, 2016

(54) INHIBITORS OF FATTY ACID AMIDE HYDROLASE AND MONOACYLGLYCEROL LIPASE FOR MODULATION OF CANNABINOID RECEPTORS

(75) Inventors: Alexandros Makriyannis, Watertown, MA (US); Lakshmipathi Pandarinathan, Shrewsbury, MA (US); Nikolai Zvonok, Revere, MA (US); Teija Parkkari, Kuopio (FI); Lauren Chapman, Waltham, MA (US)

(73) Assignee: NORTHEASTERN UNIVERSITY, Boston, MA (US)

( * ) Notice: Subject to any disclaimer, the term of this patent is extended or adjusted under 35 U.S.C. 154(b) by 779 days.

(21) Appl. No.: 12/933,322

(22) PCT Filed: Mar. 17, 2009

(86) PCT No.: PCT/US2009/037434
§ 371 (c)(1),
(2), (4) Date: Mar. 22, 2011

(87) PCT Pub. No.: WO2009/117444
PCT Pub. Date: Sep. 24, 2009

(65) Prior Publication Data
US 2011/0166138 A1  Jul. 7, 2011

Related U.S. Application Data

(60) Provisional application No. 61/037,221, filed on Mar. 17, 2008.

(51) Int. Cl.
| C07D 233/90 | (2006.01) |
| A61K 31/41 | (2006.01) |
| A61K 31/415 | (2006.01) |
| C07D 231/12 | (2006.01) |
| C07D 233/56 | (2006.01) |
| C07D 235/08 | (2006.01) |
| C07D 249/08 | (2006.01) |
| C07D 249/18 | (2006.01) |
| C07D 263/22 | (2006.01) |
| C07D 401/12 | (2006.01) |
| C07D 471/04 | (2006.01) |
| C07D 473/00 | (2006.01) |
| C07D 473/28 | (2006.01) |
| G01N 21/64 | (2006.01) |

(52) U.S. Cl.
CPC .............. *A61K 31/41* (2013.01); *A61K 31/415* (2013.01); *C07D 231/12* (2013.01); *C07D 233/56* (2013.01); *C07D 235/08* (2013.01); *C07D 249/08* (2013.01); *C07D 249/18* (2013.01); *C07D 263/22* (2013.01); *C07D 401/12* (2013.01); *C07D 471/04* (2013.01); *C07D 473/00* (2013.01); *C07D 473/28* (2013.01); *G01N 21/6428* (2013.01)

(58) Field of Classification Search
None
See application file for complete search history.

(56) References Cited

U.S. PATENT DOCUMENTS

| 4,973,588 A * | 11/1990 | Kihara et al. .............. 514/235.8 |
| 6,797,824 B2 * | 9/2004 | Thurkauf et al. ............. 544/295 |
| 2005/0014765 A1 * | 1/2005 | Mailliet et al. ........... 514/254.02 |
| 2006/0100208 A1 | 5/2006 | Makriyannis et al. |
| 2007/0203209 A1 | 8/2007 | Bartolini et al. |

OTHER PUBLICATIONS

Wermuth, Camille. Molecular Variations Based on Isoteric Replacements. The Practice of Medicinal Chemistry. Academic Press, 1996. pp. 203-237.*
Dinsmore, Christopher. Bioorganic & Medicinal Chemistry Letters 11 (2001) 537-540.*
Oddo, B. Mem. accad. Lincei [v], (1923), 14, 510-623 (STN Abstract).*
Patani, George. Chem. Rev. 96 (1996) 3147-3176.*
Saario, S. and Laitinen, J. "Therapeutic Potential of Endocannabinoid-Hydrolysing Enzyme Inhibitors," Basic & Clin. Pharmacol. Toxicol. 101:287-292 (2007).
Jhaveri et al.,"Endocannabinoid metabolism and uptake: novel targets for neuropathic and inflammatory pain," Brit. J. Pharmacol. 152:624-632 (2007).
Karanian et al., "Endocannabinoid Enhancement Protects against Kainic Acid-Induced Seizures and Associated Brain Damage," J Pharmacol. Expt. Thera. 322:1059-1066 (2007).
Scherma et al., "The endogenous cannabinoid anandamide has effects on motivation and anxiety that are revealed by fatty acid amide hydrolase (FAAH) inhibition," Neuorophmarmacol. 54:129-140 (2008).
March, Advanced Organic Chemistry: Reactions, Mechanisms and Structures, 4th Ed. John Wiley & Sons, pp. 69-74 (1992).
Antoline, et al., *Science of Synthesis. Houben-Weyl Methods of Molecular Transformations*, Georg Thieme Verlag, Stuttgart, New York (2005) (46 pgs.).
Andrushko, V. and Andrushko, N. (ed), *Stereoselective Synthesis of Drugs and Natural Products*, vol. 1, John Wiley & Sons, Inc. (2013)(49 pgs.).

(Continued)

*Primary Examiner* — Golam M M Shameem
*Assistant Examiner* — Laura Daniel
(74) *Attorney, Agent, or Firm* — Wilmer Cutler Pickering Hale and Dorr LLP

(57) ABSTRACT

Disclosed are compounds and compositions that inhibit the action of fatty acid amide hydrolase (FAAH) and monoacylglycerol lipase (MGL), methods of inhibiting FAAH and MGL, methods of modulating cannabinoid receptors, and methods of treating various disorders related to modulation of cannabinoid receptors.

1 Claim, 2 Drawing Sheets

(56) References Cited

OTHER PUBLICATIONS

Clark, J., "Structural Isomerism," Downloaded from http://www.chemguide.co.uk/basicorg/isomerism/structural.html (2000, modified Nov. 2012) (5 pgs.).

Fiske, C., "The Hydrolysis of Amides in the Animal Body. The Comparative Stability of Surface Active Homologs in Relation to the Mechanism of Enzyme Action," J. Biol. Chem., vol. 55, pp. 191-220 (1923).

Functional Isomers, OChemPal, 2009 (1 pg.).

Jones, M. Jr., *Organic Chemistry*, Princeton University, by W.W. Norton & Company, New York, NY, 1997 (6 pgs.).

Positional Isomers, Downloaded from http://science.uvu.edu/ochem/index.php/alphabetical/o-p/positional-isomers/ on Feb. 5, 2015 (2 pg.).

International Search Report and Written Opinion issued by the U.S. Patent and Trademark Office as International Searching Authority for International Application No. PCT/US09/37434 mailed Jun. 26, 2009 (8 pgs.).

* cited by examiner

Figure 1    Seizure Protection

Figures 1A - 1B are graphic representations of seizure protection.

Figures 2A - 2C are graphic representations showing that animals received either vehicle, Compound 1 or Compound 2 (5 mg/kg), immediately following KA administration.

INHIBITORS OF FATTY ACID AMIDE HYDROLASE AND MONOACYLGLYCEROL LIPASE FOR MODULATION OF CANNABINOID RECEPTORS

PRIORITY STATEMENT

This application claims the benefit of U.S. Provisional Application No. 61/037,221, filed Mar. 17, 2008. The entire disclosure of that application is relied on and incorporated into this application by reference.

FIELD OF THE INVENTION

The present disclosure relates generally to the fields of medicinal chemistry and receptor biology. More particularly, the disclosure relates to the use of certain chemical compounds in methods for treating pain, inflammation, neuropathy, neurodegenerative disease, anxiety disorder, motor function disorder, fertility disorder, appetite disorder, metabolic disorder, movement disorder, and cancer.

BACKGROUND

Presently, two $G_{i/o}$ protein coupled cannabinoid receptors have been characterized in mammals and other organisms: CB1, a receptor found in the mammalian brain and a number of other sites in peripheral tissues; and CB2, a peripheral receptor found principally in cells related to the immune system. Compounds known as cannabinergic ligands bind to, and thereby modulate, CB1 and/or CB2 receptors in a subject. Such modulation of CB1 and/or CB2 receptors can produce numerous physiological effects in a subject. In vitro methods for assaying the ability of a compound to bind to CB1 and/or CB2 receptors are known, and results from these assays correlate with, and predict, the in vivo ability of that compound to bind to CB1 and/or CB2 receptors.

Despite having a rapid onset of action, the magnitude and duration of in vivo CB1 and/or CB2 receptor modulation by cannabinergic ligands are relatively short, because of a rapid inactivation process comprising hydrolysis of that cannabinergic ligand. Fatty acid amide hydrolase (FAAH) and monoacylglycerol lipase (MGL) are two enzymes responsible for the termination of endocannabinoid signaling. FAAH (also referred to as anandamide amidase (AEAase) and anandamide amidohydrolase (AAH)), is an intracellular membrane-bound enzyme that degrades and inactivates members of the endocannabinoid class of signaling lipids such as anandamide(arachidonoyl ethanolamine). FAAH belongs to the amidase signature (AS) super family of serine hydrolases and, in contrast to the classical serine-histidine-aspartate triad found in most serine hydrolases, the catalytic machinery of this enzyme is a serine-serine-lysine catalytic triad. FAAH has been isolated, molecularly cloned and its 2.8 Å crystal structure was recently reported.

FAAH can not only hydrolyze anandamide into arachidonic acid and ethanolamine but it can also catalyze its reverse synthesis from the two hydrolysis components. FAAH can also hydrolyze several bioactive fatty acid amides not belonging to the endocannabinoid family, including, but not limited to, the sleep inducing lipid oleamide, the appetite-suppressing agent oleoylethanolamine, the related 1-oleoylglycerol and 2-oleoylglycerol, and the peripheral analgesic and anti-inflammatory mediator palmitoylethanolamine. In general, FAAH can hydrolyze a range of fatty acid amides, ethanolamides, esters, arachidonoyl substrates, and oleoyl substrates, as well as other substrates.

Although FAAH has been shown to catalyze hydrolysis of 2-arachidonoylglycerol (another endogenous cannabinergic ligand) in vitro, MGL plays the predominant role in catalyzing 2-AG hydrolysis in vivo. MGL (also known as MGL, MAG lipase or MAGL) is a serine hydrolase that converts 2- and 1-monoglycerides to fatty acid and glycerol.

The physiological responses that result from modulation of cannabinoid receptors have recognized therapeutic potential. (see Saario and Laitinen (2007) Basic & Clin. Pharmacol. Toxicol. 101:287-292; Jhaveri et al. (2007) Brit. J. Pharmacol. 152:624-632; Karanian et al. (2007) J. Pharmacol. Expt. Thera. 322:1059-1066; Scherma et al. (2008) Neuorophmarmacol. 54:129-140. However, the effectiveness of these responses is limited and short-lived due to the hydrolytic activity of FAAH and MGL.

A need, therefore, exists for compounds that inhibit the hydrolytic activity of FAAH and/or MGL, thereby maintaining or increasing the magnitude and duration of cannabinoid receptor modulation.

SUMMARY OF THE INVENTION

It has been discovered that certain chemical compounds can inhibit FAAH and MGL. This discovery has been exploited to develop the present application, which includes novel compounds and therapeutic compositions for inhibiting FAAH and MGL, methods for modulating cannabinoid receptors, methods for treating various disorders in a subject, and a new substrate for fluorogenic assays.

One aspect of the application is directed to a method of modulating cannabinoid receptors in a biological sample. In this method, the level of a cannabinergic ligand in the biological sample is measured. The biological sample is then contacted with a compound of Formula (I), thereby inhibiting an enzyme that hydrolyzes the cannabinergic ligand. The level of the cannabinergic ligand in the contacted sample is then measured, the cannabinoid receptors being modulated if the level of the cannabinergic ligand in the contacted sample is the same or greater than the level of the cannabinergic ligand in the uncontacted sample.

In the compound having Formula (I), R—X—Y, Y is selected from the group consisting of:

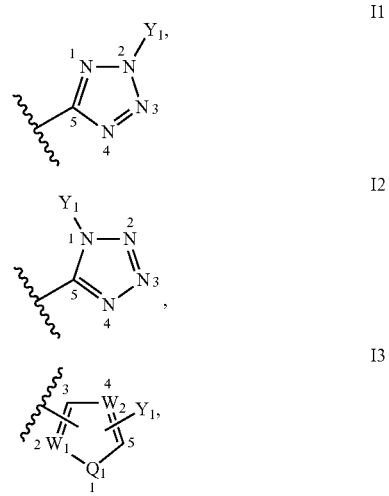

-continued

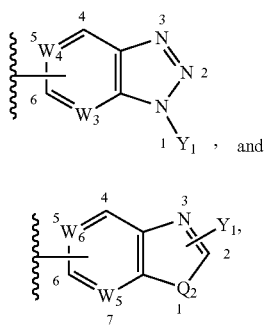

wherein:
W₁ is either CH or N if it is not bonded to X or Y₁, or W₁ is C if it is bonded to X or Y₁; if W₁ is N, then it can occupy position 2, 3, 4, or 5 in I 3;
W₂ is either CH or N if it is not bonded to X or Y₁, or W₂ is C if it is bonded to X or Y₁; if W₂ is N, then it can occupy position 2, 3, 4, or 5 in I 3;
W₃ is CH or N if it is not bonded to X, or W₃ is C if it is bonded to X; if W₃ is N then it can occupy position 4, 5, 6, or 7 in I 4;
W₄ is CH or N if it is not bonded to X, or W₄ is C if it is bonded to X; if W₄ is N then it can occupy position 4, 5, 6, or 7 in I 4;
W₅ is CH or N if it is not bonded to X, or W₅ is C if it is bonded to X; if W₅ is N then it can occupy position 4, 5, 6, or 7 in I 5;
W₆ is CH or N if it is not bonded to X, or W₆ is C if it is bonded to X; if W₆ is N then it can occupy position 4, 5, 6, or 7 in I 5;
Q₁ is CH₂, O, or NH if Q₁ is not bonded to X or Y₁, or Q₁ is CH or N if Q₁ is bonded to X or Y₁;
Q₂ is CH₂ or NH if Q₂ is not bonded to Y₁, or Q₂ is CH or N if Q₂ is bonded to Y₁;
Y₁ is selected from the group consisting of:

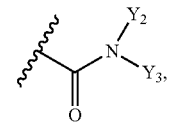

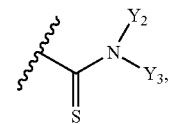

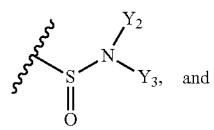

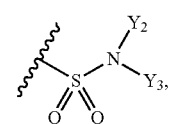

wherein:
Y₂ and Y₃ are each independently H, alkyl, cycloalkyl, aryl, heteroaryl, —C₁₋₅-alkyl-Y₄, -cycloalkyl-Y₄, -aryl-Y₄, or -heteroaryl-Y₄, or Y₂ and Y₃ together comprise part of a 5-7 membered saturated heterocyclic ring which can be substituted or unsubstituted and can contain up to one additional heteroatom selected from the group consisting of N, O, and S, with or without substitution on the heteroatom wherein the substituent is alkyl, aryl, heteroaryl, alkyl-aryl or alkyl-heteroaryl;
Y₄ is —F, —Cl, Br, —I, —OH, —SH, —NH₂, —CN, —N₃, —NCS, —CONH₂, —CONR₁₃R₁₄, —SO₂NR₁₃R₁₄, —COOH, —COOMe, —COOEt, COCF₃, —NO₂, —CF₃, —SO₃H, SO₂R₁₃, —P(O)(OH)₂, —PO(OR₁)₂, —C≡CH, or —CH=CH₂;
R₁₃ and R₁₄ are each independently H or C₁-C₅-alkyl;
wherein:
X is —(CH₂)ₙ— or —(CH₂)ⱼ-A-(CH₂)ₖ—, wherein:
A is —CH=CH—, —C=O, O, S, NH, —C(O)NH, —NHC=O, —NHC(O)NH—, OC(O)NH—, NHC(O)O, or —OC(O)O—;
n is an integer from 0 to 15;
j is an integer from 0 to 10;
k is an integer from 0 to 10;
and if n, j, or k is independently 0 the structural portion modified by that integer is absent and the adjacent subunits are directly connected;
wherein:
R is selected from the group consisting of:

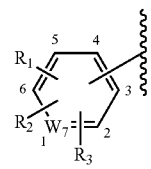

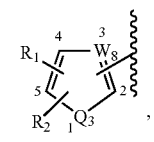

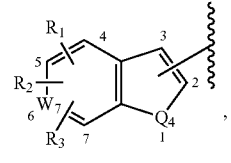

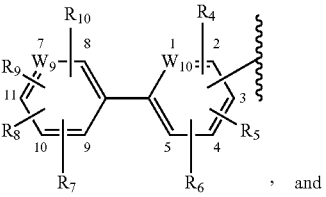

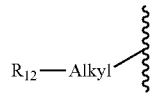

wherein:
W₇ is CH or N if W₇ is not bonded to X, R₁, R₂, or R₃, or W₇ is C if W₇ is bonded to X, R₁, R₂, or R₃; if W₇ is N then it can occupy position 1, 2, 3, 4, 5 or 6 in I 10 and 4, 5, 6 or 7 in I 12;

$W_8$ is CH or N if $W_8$ is not bonded to X, $R_1$, or $R_2$, or $W_8$ is C if $W_8$ is bonded to X, $R_1$, or $R_2$; if $W_8$ is N then it can occupy position 2, 3, 4 or 5 in I 11;

$W_9$ is CH or N if $W_9$ is not bonded to $R_7$, $R_8$, $R_9$, or $R_{10}$, or $W_9$ is C if $W_9$ is bonded to $R_7$, $R_8$, $R_9$, or $R_{10}$; if $W_9$ is N then it can occupy position 7, 8, 9, 10, or 11 in I 13;

$W_{10}$ is CH or N if $W_{10}$ is not bonded to X, $R_4$, $R_5$, or $R_6$, or $W_{10}$ is C if $W_{10}$ is bonded to X, $R_4$, $R_5$, or $R_6$; if $W_{10}$ is N then it can occupy position 1, 2, 3, 4, or 5 in I 13;

$Q_3$ is $CH_2$, O, S, or NH if $Q_3$ is not bonded to X, $R_1$, $R_2$, or $Q_3$ is CH or N if $Q_3$ is bonded to X, $R_1$, $R_2$;

$Q_4$ is $CH_2$, O, S, or NH if $Q_4$ is not bonded to X, or $Q_4$ is CH or N if $Q_4$ is bonded to X;

$R_1$, $R_2$, $R_3$, $R_4$, $R_5$, $R_6$, $R_7$, $R_8$, $R_9$, and $R_{10}$ are each independently —H, —F, —Cl, —Br, —I, —OH, —OAc, —SH, —NH$_2$, —CN, —N$_3$, —NCS, —CONH$_2$, —SO$_2$NH$_2$, —COOH, —NO$_2$, —CHO, —CF$_3$, —OCF$_3$, —SO$_3$H, —SO$_2$F, —O—P(O)(OH)$_2$, —O—P(O)(O-alkyl)$_2$, —O—P(O)(OH)(O-alkyl), —P(O)(O-alkyl)$_2$, —P(O)(OH)(O-alkyl), —Sn(alkyl)$_3$, —Si(alkyl)$_3$, —C≡CH, —CH=CH$_2$, -alkyl-R$_{12}$, or —Z-alkyl-R$_{12}$;

Z is —O—, —S—, —NH—, —C(O)—, —C(O)O—, —OC(O)—, —C(O)NH—, —NHC(O)—, —S(O)—, —S(O)$_2$—, —SO$_2$NH—, —NHSO$_2$—, —SO$_2$O—, or —OSO$_2$—;

$R_{12}$ is —H, —F, —Cl, —Br, —I, —OH, —OAc, —SH, —NH$_2$, —CN, —N$_3$, —NCS, —CONH$_2$, —SO$_2$NH$_2$, —COOH, —NO$_2$, —CHO, —CF$_3$, —OCF$_3$, —SO$_3$H, —SO$_2$F, —O—P(O)(OH)$_2$, —Sn(alkyl)$_3$, —Si(alkyl)$_3$, —OSi(alkyl)$_3$, —C≡CH, —CH$_2$—C≡CH and —CH=CH$_2$;

wherein:

if Y is I 1 or I 2 where $Y_1$ is —C(O)—N(CH$_3$)$_2$ and X is —(CH$_2$)$_n$— where n=1; then R can not be 1,1'-biphenyl-4-yl, 4-fluorophenyl, or 3-iodo-4-azidophenyl.

In some embodiments, the enzyme inhibited by the compound of Formula (I) is FAAH and/or MGL.

In certain embodiments, the cannabinergic ligand is anandamide or 2-arachidonoylglycerol.

In some embodiments, the CB1 receptor or the CB2 receptor is modulated.

In still further embodiments, the compound having formula R—X—Y in the method of modulation is a compound listed in Table 2, 3, and 4 below.

A further aspect of this application is directed to a method of treating a neuropathy in a subject. In this method, a therapeutically effective amount of a compound of Formula (I) is administered to the subject. The administration of the compound treats the neuropathy of the subject. The administration of the compound treats the neuropathy of the subject. In some embodiments, the neuropathy is inflammation, pain, neuropathic pain, neuropathic low back pain, complex regional pain syndrome, post trigeminal neuralgia, causalgia, toxic neuropathy, reflex sympathetic dystrophy, diabetic neuropathy, chronic neuropathy caused by chemotherapeutic agents, central pain, peripheral pain, pellagric neuropathy, alcoholic neuropathy, Beriberi neuropathy, or burning feet syndrome. In particular embodiments, the compound of Formula (I) is a compound listed in Table 1 below.

In yet other embodiments, the neuropathy is a neurodegenerative disease. In particular embodiments, the neurodegenerative disease is multiple sclerosis, Parkinson's disease, Huntington's chorea, Alzheimer's disease, amyotrophic lateral sclerosis, memory disorder, mood disorder, sleep disorder, gastrointestinal motility disorder, irritable bowel syndrome, diarrhea, cardiovascular disease, hypertension, osteoporosis, osteoarthritis, emesis, epilepsy, a mental disorder, schizophrenia, depression, glaucoma, cachexia, insomnia, traumatic brain injury, spinal cord injury, seizures, excitotoxin exposure, ischemia, or AIDS wasting syndrome.

An additional aspect of the application is directed to a method of treating a motor function disorder in a subject. The method comprises administering to the subject a therapeutically effective amount of a compound of Formula (I). The administration of the compound treats the motor function disorder of the subject. In one embodiment, the motor function disorder is Tourette's syndrome. In particular embodiments, the compound of Formula (I) is a compound listed in Table 1 below.

Another aspect of the application is directed to a method of treating an anxiety disorder in a subject. The method comprises administering to the subject a therapeutically effective amount of a compound of Formula (I). The administration of the compound treats the anxiety disorder of the subject. In certain embodiments, the anxiety disorder is panic disorder, acute stress disorder, post-traumatic stress disorder, substance-induced anxiety disorder, obsessive compulsive disorder, agoraphobia, specific phobia, or social phobia. In particular embodiments, the compound of Formula (I) is a compound listed in Table 1 below.

An additional aspect of the disclosure is directed to a method of treating a fertility disorder in a subject. The method comprises administering to the subject a therapeutically effective amount of a compound of Formula (I). The administration of the compound treats the fertility disorder of the subject. In particular embodiments, the compound of Formula (I) is a compound listed in Table 1 below.

In yet another aspect, the disclosure is directed to a method of treating an appetite disorder in a subject. The method comprises administering to the subject a therapeutically effective amount of a compound of Formula (I). The administration of the compound treats the appetite disorder, the metabolic disorder, or the movement disorder of the subject. In particular embodiments, the compound of Formula (I) is a compound listed in Table 1 below.

In another aspect, the disclosure is directed to a method of treating a metabolic disorder in a subject. The method comprises administering to the subject a therapeutically effective amount of a compound of Formula (I). The administration of the compound treats the metabolic disorder of the subject. In particular embodiments, the compound of Formula (I) is a compound listed in Table 1 below.

In still another aspect, the disclosure is directed to a method of treating a movement disorder in a subject. The method comprises administering to the subject a therapeutically effective amount of a compound of Formula (I). The administration of the compound treats the movement disorder of the subject. In particular embodiments, the compound of Formula (I) is a compound listed in Table 1 below.

Another aspect of the disclosure is directed to a method of treating cancer in a subject. The method comprising administering to the subject a therapeutically effective amount of a compound of Formula (I). The administration of the compound treats the cancer of the subject. In particular embodiments, the compound of Formula (I) is a compound listed in Table 1 below.

Another aspect of the invention is directed to certain chemical compounds of Formula (I), R—X—Y, wherein Y is selected from the group consisting of:

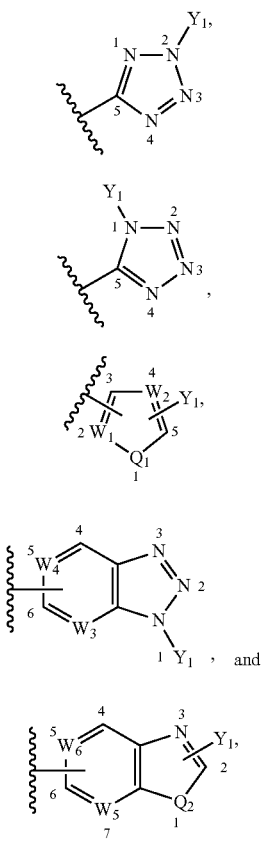

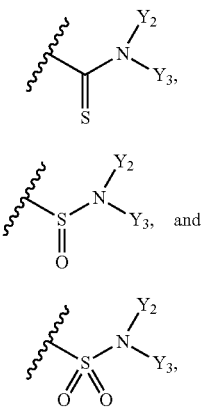

wherein:
- W₁ is either CH or N if it is not bonded to X or Y₁, or W₁ is C if it is bonded to X or Y₁; if W₁ is N, then it can occupy position 2, 3, 4, or 5 in I 3;
- W₂ is either CH or N if it is not bonded to X or Y₁, or W₂ is C if it is bonded to X or Y₁; if W₂ is N, then it can occupy position 2, 3, 4, or 5 in I 3;
- W₃ is CH or N if it is not bonded to X, or W₃ is C if it is bonded to X; if W₃ is N then it can occupy position 4, 5, 6, or 7 in I 4;
- W₄ is CH or N if it is not bonded to X, or W₄ is C if it is bonded to X; if W₄ is N then it can occupy position 4, 5, 6, or 7 in I 4;
- W₅ is CH or N if it is not bonded to X, or W₅ is C if it is bonded to X; if W₅ is N then it can occupy position 4, 5, 6, or 7 in I 5;
- W₆ is CH or N if it is not bonded to X, or W₆ is C if it is bonded to X; if W₆ is N then it can occupy position 4, 5, 6, or 7 in I 5;
- Q₁ is CH₂, O, or NH if Q₁ is not bonded to X or Y₁, or Q₁ is CH or N if Q₁ is bonded to X or Y₁;
- Q₂ is CH₂ or NH if Q₂ is not bonded to Y₁, or Q₂ is CH or N if Q₂ is bonded to Y₁;
- Y₁ is selected from the group consisting of:

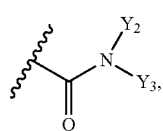

wherein
- Y₂ and Y₃ are each independently H, alkyl, cycloalkyl, aryl, heteroaryl, —C₁₋₅-alkyl-Y₄, -cycloalkyl-Y₄, -aryl-Y₄, or -heteroaryl-Y₄, or Y₂ and Y₃ together comprise part of a 5-7 membered saturated heterocyclic ring which can be substituted or unsubstituted and can contain up to one additional heteroatom selected from the group consisting of N, O, and S, with or without substitution on the heteroatom wherein the substituent is alkyl, aryl, heteroaryl, alkyl-aryl or alkyl-heteroaryl;
- Y₄ is —F, —Cl, Br, —I, —OH, —SH, —NH₂, —CN, —N₃, —NCS, —CONH₂, —CONR₁₃R₁₄, —SO₂NR₁₃R₁₄, —COOH, —COOMe, —COOEt, COCF₃, —NO₂, —CF₃, —SO₃H, SO₂R₁₃, —P(O)(OH)₂, —PO(OR₁)₂, —C≡CH, or —CH=CH₂;
- R₁₃ and R₁₄ are each independently H or C₁-C₅-alkyl;

wherein:
- X is —(CH₂)ₙ— or —(CH₂)ⱼ-A-(CH₂)ₖ—, wherein:
- A is —CH=CH—, —C=O, O, S, NH, —C(O)NH, —NHC=O, —NHC(O)NH—, OC(O)NH—, NHC(O)O, or —OC(O)O—;
- n is an integer from 0 to 15;
- j is an integer from 0 to 10;
- k is an integer from 0 to 10;
- and if n, j, or k is independently 0 the structural portion modified by that integer is absent and the adjacent subunits are directly connected;

wherein:
R is selected from the group consisting of:

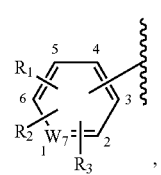

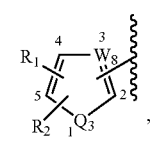

-continued

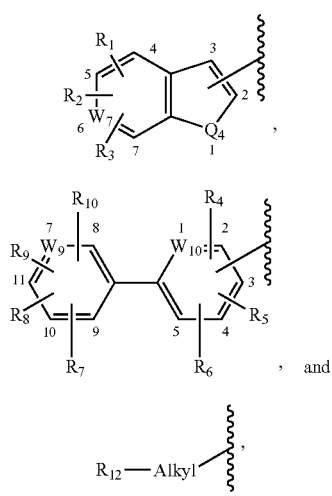

In certain embodiments, the compound is

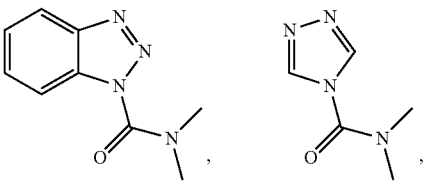

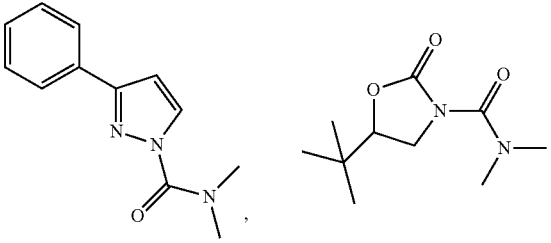

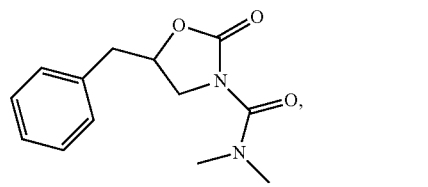

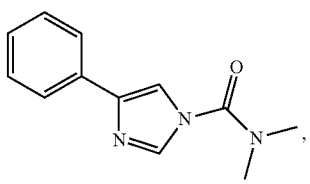

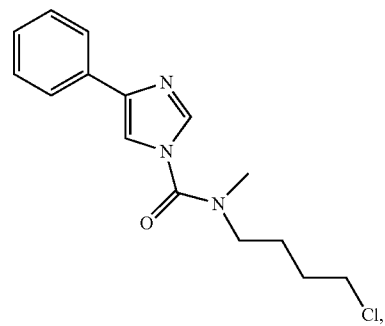

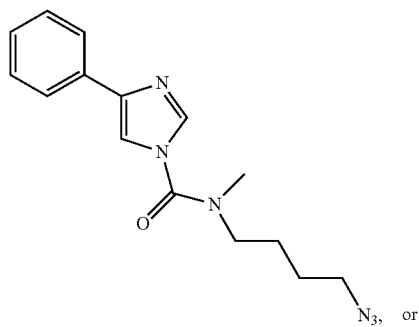

wherein:

$W_7$ is CH or N if $W_7$ is not bonded to X, $R_1$, $R_2$, or $R_3$, or $W_7$ is C if $W_7$ is bonded to X, $R_1$, $R_2$, or $R_3$; if $W_7$ is N then it can occupy position 1, 2, 3, 4, 5 or 6 in I 10 and 4, 5, 6 or 7 in I 12;

$W_8$ is CH or N if $W_8$ is not bonded to X, $R_1$, or $R_2$, or $W_8$ is C if $W_8$ is bonded to X, $R_1$, or $R_2$; if $W_8$ is N then it can occupy position 2, 3, 4 or 5 in I 11;

$W_9$ is CH or N if $W_9$ is not bonded to $R_7$, $R_8$, $R_9$, or $R_{10}$, or $W_9$ is C if $W_9$ is bonded to $R_7$, $R_8$, $R_9$, or $R_{10}$; if $W_9$ is N then it can occupy position 7, 8, 9, 10, or 11 in I 13;

$W_{10}$ is CH or N if $W_{10}$ is not bonded to X, $R_4$, $R_5$, or $R_6$, or $W_{10}$ is C if $W_{10}$ is bonded to X, $R_4$, $R_5$, or $R_6$; if $W_{10}$ is N then it can occupy position 1, 2, 3, 4, or 5 in I 13;

$Q_3$ is $CH_2$, O, S, or NH if $Q_3$ is not bonded to X, $R_1$, $R_2$, or $Q_3$ is CH or N if $Q_3$ is bonded to X, $R_1$, $R_2$;

$Q_4$ is $CH_2$, O, S, or NH if $Q_4$ is not bonded to X, or $Q_4$ is CH or N if $Q_4$ is bonded to X;

$R_1$, $R_2$, $R_3$, $R_4$, $R_5$, $R_6$, $R_7$, $R_8$, $R_9$, and $R_{10}$ are each independently —H, —F, —Cl, —Br, —I, —OH, —OAc, —SH, —$NH_2$, —CN, —$N_3$, —NCS, —$CONH_2$, —$SO_2NH_2$, —COOH, —$NO_2$, —CHO, —$CF_3$, —$OCF_3$, —$SO_3H$, —$SO_2F$, —O—$P(O)(OH)_2$, —O—$P(O)(O\text{-alkyl})_2$, —O—P(O)(OH)(O-alkyl), —$P(O)(O\text{-alkyl})_2$, —P(O)(OH)(O-alkyl), —Sn(alkyl)$_3$, —Si(alkyl)$_3$, —C≡CH, —CH=$CH_2$, -alkyl-$R_{12}$, or —Z-alkyl-$R_{12}$;

Z is —O—, —S—, —NH—, —C(O)—, —C(O)O—, —OC(O)—, —C(O)NH—, —NHC(O)—, —S(O)—, —S(O)$_2$—, —$SO_2$NH—, —$NHSO_2$, —$SO_2$O—, or —$OSO_2$—;

$R_{12}$ is —H, —F, —Cl, —Br, —I, —OH, —OAc, —SH, —$NH_2$, —CN, —$N_3$, —NCS, —$CONH_2$, —$SO_2NH_2$, —COOH, —$NO_2$, —CHO, —$CF_3$, —$OCF_3$, —$SO_3H$, —$SO_2F$, —O—$P(O)(OH)_2$, —Sn(alkyl)$_3$, —Si(alkyl)$_3$, —OSi(alkyl)$_3$, —C≡CH, —$CH_2$—C≡CH and —CH=$CH_2$; and wherein:

if Y is I 1 or I 2 where $Y_1$ is —C(O)—N(CH$_3$)$_2$ and X is —(CH$_2$)$_n$— where n=1; then R can not be 1,1'-biphenyl-4-yl, 4-fluorophenyl, or 3-iodo-4-azidophenyl.

-continued

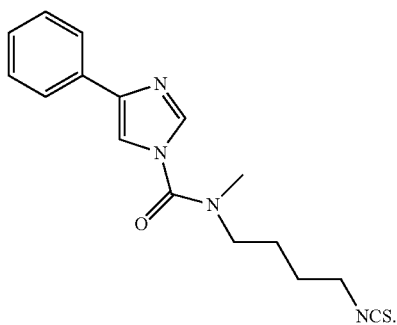

In other embodiments, the compound is

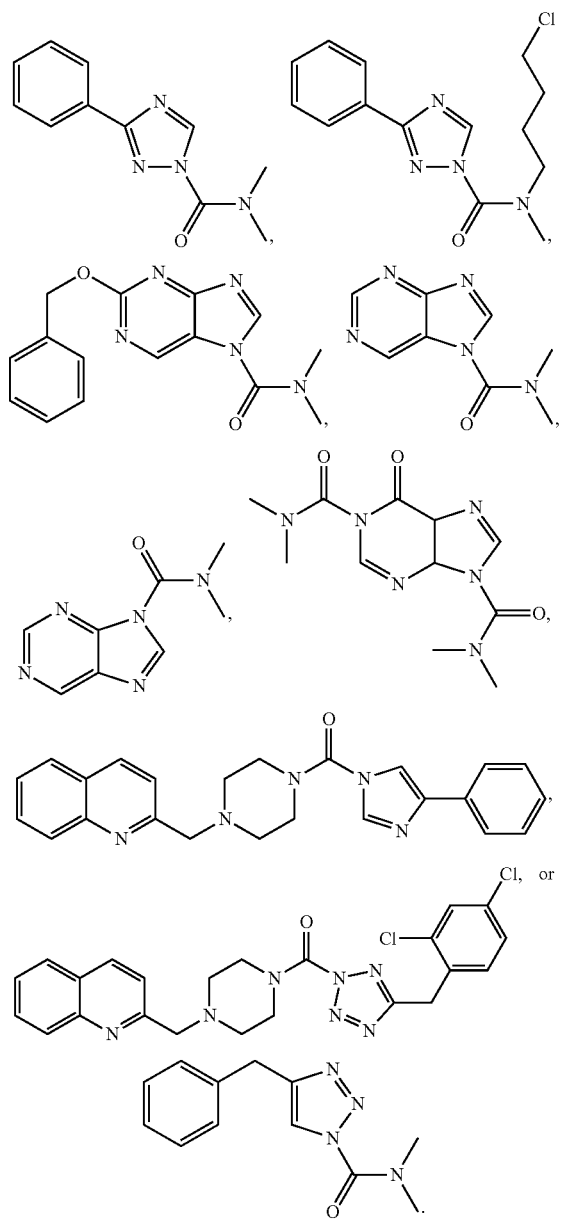

In still further embodiments, the compound is

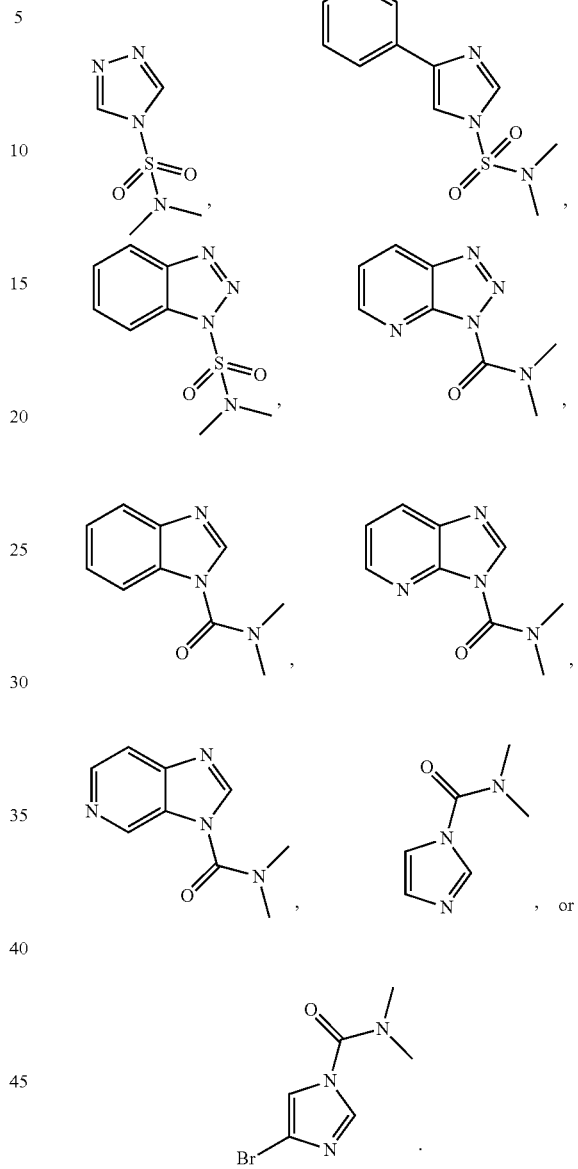

In particular embodiments, R and X in the compounds of Formula (I) are as defined above and $Y_1$ is —$CONY_2Y_3$ where $Y_2$ and $Y_3$ together comprise part of a 5-7 membered saturated heterocyclic ring which can be substituted or unsubstituted and can contain up to one additional heteroatom selected from the group consisting of N, O, and S, with a substituent on the heteroatom wherein the substituent is aryl, heteroaryl, alkyl-aryl, or alkyl-heteroaryl. In other embodiments, R is I 13.

Still another aspect of this application is directed to a pharmaceutical composition comprising at least one compound of Formula (I) and a pharmaceutically acceptable carrier therefore.

Another aspect of this application provides a novel substrate that fluoresces when hydrolyzed by MGL, wherein the substrate is a compound of the formula:

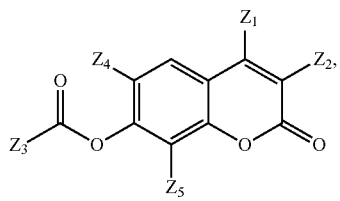

wherein $Z_1$ and $Z_2$ are each independently H, alkyl, cycloalkyl, aryl, or heteroaryl, or $Z_1$ and $Z_2$ together comprise part of a 5 or 6 membered saturated heterocyclic ring. $Z_3$ is alkyl, aryl, or —$(CH_2)_n$—$(CH=CH)_m$—$(CH_2)_o$—$(CH=CH)_p$—$(CH_2)_q$—$CH_3$, wherein n, m, o, p, q=0-6. $Z_3$ is selected from essential and non-essential fatty acid alkyl chain. $Z_4$ and $Z_5$ are each independently H, alkyl, aryl, —O-alkyl, or —NH-alkyl.

A further aspect of this application is directed a method of detecting the presence of a MGL in a sample. In this method, a sample containing MGL is contacted with a fluorogenic substrate of formula:

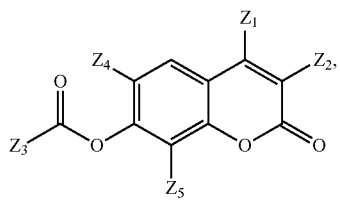

wherein $Z_1$ and $Z_2$ are each independently H, alkyl, cycloalkyl, aryl, or heteroaryl, or $Z_1$ and $Z_2$ together comprise part of a 5 or 6 membered saturated heterocyclic ring. $Z_3$ is alkyl, aryl, or —$(CH_2)_n$—$(CH=CH)_m$—$(CH_2)_o$—$(CH=CH)_p$—$(CH_2)_q$—$CH_3$, wherein n, m, o, p, q=0-6. $Z_3$ is selected from essential and non-essential fatty acid alkyl chain. $Z_4$ and $Z_5$ are each independently H, alkyl, aryl, —O-alkyl, or —NH-alkyl.

In some embodiments, the fluorogenic substrate is arachidonyl-7-hydroxy-6-methoxy-4-methyl-coumarin ester.

The contacting step continues for a sufficient time to allow any monoacylglycerol lipase present in the sample to hydrolyze the fluorogenic substrate, thereby producing a fluorescent product. Then, presence of the fluorescent product is detected in the sample. The presence of fluorescent product is indicative of the presence of a monoacylglycerol lipase in the sample.

In some embodiments, the fluorogenic substrate is arachidonyl-7-hydroxy-6-methoxy-4-methyl-coumarin ester.

In some embodiments, the method further comprises the step of measuring the amount of fluorescent product formed in the sample. The amount of fluorescent product is indicative of the amount of MGL activity in the sample.

In certain embodiments, the sample is a biological sample.

Yet another aspect of this application is directed to a method of identifying a compound that inhibits MGL activity. In this method, a first MGL-containing sample is obtained. Next, the sample is contacted with a test compound for a time sufficient to allow the test compound to bind to the monoacylglyercol lipase. Then, the sample is further contacted with a fluorogenic substrate of the formula:

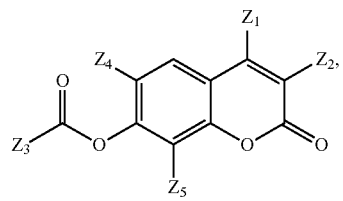

wherein $Z_1$ and $Z_2$ are each independently H, alkyl, cycloalkyl, aryl, or heteroaryl, or $Z_1$ and $Z_2$ together comprise part of a 5 or 6 membered saturated heterocyclic ring. $Z_3$ is alkyl, aryl, or —$(CH_2)_n$—$(CH=CH)_m$—$(CH_2)_o$—$(CH=CH)_p$—$(CH_2)_q$—$CH_3$, wherein n, m, o, p, q=0-6. $Z_3$ is selected from essential and non-essential fatty acid alkyl chain. $Z_4$ and $Z_5$ are each independently H, alkyl, aryl, —O-alkyl, or —NH-alkyl.

This further contacting step continues for a time sufficient to allow any unbound monoacylglycerol lipase in the sample to hydrolyze the fluorogenic substrate. A fluorescent product is formed by this hydrolysis. Next, an amount of fluorescent product formed is detected. Finally, the amount of fluorescent product formed is compared to an amount of fluorescent product formed in a control sample that does not contain the test compound. The test compound is an inhibitor of MGL activity if the amount of fluorescent product in the first sample is detectably less than in the control sample.

In some embodiments, the fluorogenic substrate is arachidonyl-7-hydroxy-6-methoxy-4-methyl-coumarin ester.

In some embodiments, the method further comprises the step of measuring the amount of fluorescent product formed in the sample. The amount of fluorescent product is indicative of the amount of MGL activity in the sample.

In certain embodiments, the sample is a biological sample.

DESCRIPTION OF THE FIGURES

The foregoing and other objects of the present application, the various features thereof, as well as the invention itself may be more fully understood from the following description, when read together with the accompanying figures in which.

DETAILED DESCRIPTION

Figure 1A:
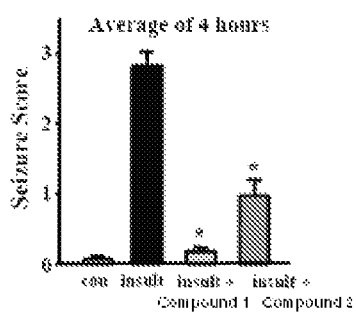
FIG. 1A is a graphic representation of seizure protection after administration of compound 1 or 2.

This application relates to compounds that inhibit FAAH or FAAH and MGL, to pharmaceutical compositions comprising these compounds, to methods for modulating cannabinoid receptors, to methods for inhibiting FAAH and MGL, and to methods for treating inflammation, pain, neuropathy, central nervous system disorders, and neurodegenerative disorders.

Throughout this application, various patents, patent applications and publications are referenced. The disclosures of these patents, patent applications and publications in their entireties are incorporated into this application by reference in order to more fully describe the state of the art as known to those skilled therein as of the date of this application. This disclosure will govern in the instance that there is any inconsistency between the patents, patent applications and publications and this disclosure.

1. DEFINITIONS

For convenience, certain terms employed in the specification, examples and claims are collected here. Unless defined otherwise, all technical and scientific terms used in this disclosure have the same meanings as commonly understood by one of ordinary skill in the art to which this disclosure belongs. The initial definition provided for a group or term provided in this disclosure applies to that group or term throughout the present disclosure individually or as part of another group, unless otherwise indicated.

The compounds of this disclosure include any and all possible isomers, stereoisomers, enantiomers, diastereomers, tautomers, pharmaceutically acceptable salts, and solvates thereof. Thus, the terms "compound" and "compounds" as used in this disclosure refer to the compounds of this disclosure and any and all possible isomers, stereoisomers, enantiomers, diastereomers, tautomers, pharmaceutically acceptable salts, and solvates thereof.

In general, the compositions of the disclosure can be alternately formulated to comprise, consist of, or consist essentially of, any appropriate components disclosed in this application. The compositions of the disclosure can additionally, or alternatively, be formulated so as to be devoid, or substantially free, of any components, materials, ingredients, adjuvants or species used in the prior art compositions or that are otherwise not necessary to the achievement of the function and/or objectives of the present disclosure.

The articles "a" and "an" are used in this disclosure to refer to one or more than one (i.e., to at least one) of the grammatical object of the article. By way of example, "an element" means one element or more than one element.

The term "or" is used in this disclosure to mean, and is used interchangeably with, the term "and/or," unless indicated otherwise.

The term "about" is used in this disclosure to mean a value − or +20% of a given numerical value. Thus, "about 60%" means a value between 60-20% of 60 and 60+20% of 60 (i.e., between 48% and 72%).

Unless otherwise specifically defined, "alcohol" refers to the general formula alkyl-OH and includes primary, secondary and tertiary variations.

Unless otherwise specifically defined, "acyl" refers to the general formula —C(O)alkyl.

Unless otherwise specifically defined, the terms "alkyl" and "alk" refer to a straight or branched chain alkane (hydrocarbon) radical, which may be fully saturated, mono- or polyunsaturated, and can include divalent radicals, having from 1 to about 15 carbon atoms. Examples of saturated hydrocarbon radicals include, but are not limited to, groups such as methyl (Me), ethyl (Et), n-propyl, isopropyl, n-butyl, t-butyl, isobutyl, sec-butyl, homologs and isomers of, for example, n-pentyl, n-hexyl, n-heptyl, n-octyl, 1,1-dimethyl-heptyl, 1,2-dimethyl-heptyl, and the like. An unsaturated alkyl group includes one or more double bonds, triple bonds or combinations thereof. Examples of unsaturated alkyl groups include but are not limited to, vinyl, propenyl, crotyl, 2-isopentenyl, allenyl, butenyl, butadienyl, pentenyl, pentadienyl, 3-(1,4-pentadienyl), hexenyl, hexadienyl, ethynyl, propynyl, butynyl, and higher homologs and isomers. The term "divalent alkyl radicals" unless otherwise specifically defined refers to the general formula: -alkyl-. The term "$C_{1-m}$-alkyl" refers to an alkyl having from 1 to about m carbon atoms. The alkyl group may be optionally substituted with one or more substituents, e.g., 1 to 5 substituents, at any available point of attachment, as defined below.

Unless otherwise specifically defined, "alkoxy" refers to the general formula —O-alkyl.

Unless otherwise specifically defined, "alkylamino" refers to the general formula —(NH)-alkyl.

Unless otherwise specifically defined, "di-alkylamino" refers to the general formula —N-(alkyl)$_2$. Unless otherwise specifically limited di-alkylamino includes cyclic amine compounds such as piperidine and morpholine.

Unless otherwise specifically defined, "aroyl" refers to the general formula —C(=O)-aryl.

Unless otherwise specifically defined, the term "aryl" refers to cyclic, aromatic hydrocarbon groups that have 1 to 5 aromatic rings, including monocyclic or bicyclic groups such as phenyl, biphenyl or naphthyl. Where containing two or more aromatic rings (bicyclic, etc.), the aromatic rings of the aryl group may be joined at a single point (e.g., biphenyl), or fused (e.g., naphthyl, phenanthrenyl and the like). The aryl group may be optionally substituted by one or more substituents, e.g., 1 to 5 substituents, at any point of attachment. In addition to the substituents described under the definition of "substituted," other exemplary substituents include, but are not limited to, nitro, cycloalkyl or substituted cycloalkyl, cycloalkenyl or substituted cycloalkenyl, cyano, alkyl, fused cyclic groups, fused cycloalkyl, fused cycloalkenyl, fused heterocycle, and fused aryl, and those groups recited above as exemplary alkyl substituents. The substituents can themselves be optionally substituted. The term "divalent aryl radicals," unless otherwise specifically defined, refers to the general formula: -aryl-.

Unless otherwise specifically defined, the term "cycloalkyl" refers to a saturated or partially saturated cyclic hydrocarbon group containing from 1 to 4 rings and 3 to 8 carbons per ring, including, for example, 4 to 7 membered monocyclic groups, 7 to 12 membered bicyclic groups, or 8 to 16 membered tricyclic ring systems, polycyclic groups, or bridged systems. Exemplary groups include, but are not limited to, cyclopropyl, cyclobutyl, cyclopentyl, cyclohexyl, cycloheptyl, adamantyl, cyclobutenyl, cyclopentenyl, and cyclohexenyl, etc. The cycloalkyl group may be optionally substituted with one or more substituents, e.g., 1 to 5 substituents, at any available point of attachment. In addition to the substituents described under the definition of "substituted," other exemplary substituents include, but are not limited to, nitro, cyano, alkyl, spiro attached or fused cyclic substituents, spiro-attached cycloalkyl, spiro-attached cycloalkenyl, spiro-attached heterocycle, fused cycloalkyl, fused cycloalkenyl, fused heterocycle, fused aryl, and those groups recited above as exemplary alkyl substituents. The substituents can themselves be optionally substituted. The term "divalent cycloalkyl radicals" unless otherwise specifically defined refers to the general formula: -cycloalkyl-.

Unless otherwise specifically defined, the term "adamantyl" includes, but is not limited to, 1 adamantyl, 2 adamantyl, and 3 adamantyl. The adamantyl group may be optionally substituted with the groups recited as exemplary cycloalkyl substituents as well as the substituents described under the definition of "substituted."

Unless otherwise specifically defined, the term "halogen" refers to fluorine, chlorine, bromine, and iodine.

Unless otherwise specifically defined, the terms "heterocycle" and "heterocyclic" refer to fully saturated, or partially or fully unsaturated, including aromatic (i.e., "heteroaryl") cyclic groups (for example, 4 to 7 membered monocyclic, 7 to 12 membered bicyclic, or 8 to 16 membered tricyclic ring systems) which have at least one heteroatom in at least one carbon atom-containing ring. Each ring of the heterocyclic group containing a heteroatom may have 1, 2, 3, or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached to the remainder of the molecule at any heteroatom or carbon atom of the ring or ring system. Exemplary monocyclic heterocyclic groups include, but are not limited to, azetidinyl, pyrrolidinyl, pyrrolyl, pyrazolyl, oxetanyl, dioxanyl, dioxolanyl, oxathiolanyl, pyrazolinyl, imidazolyl, imidazolinyl, imidazolidinyl, oxazolyl, oxazolidinyl, isoxazolinyl, isoxazolyl, thietanyl, azetidine, diazetidine, thiolanyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, hexahydrodiazepinyl, 4-piperidonyl, pyridyl, purinyl, pyrazinyl, pyrimidinyl, pyridazinyl, triazinyl, triazolyl, tetrazolyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, and the like. Exemplary bicyclic heterocyclic groups include, but are not limited to, indolyl, isoindolyl, benzothiazolyl, benzoxazolyl, benzoxadiazolyl, benzothienyl, benzo[d][1,3]dioxolyl, 2,3-dihydrobenzo[b][1,4]dioxinyl, quinuclidinyl, quinolinyl, tetrahydroisoquinolinyl, isoquinolinyl, benzimidazolyl, benzopyranyl, indolizinyl, benzofuryl, benzofurazanyl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), triazinylazepinyl, tetrahydroquinolinyl and the like. Exemplary tricyclic heterocyclic groups include, but are not limited to, carbazolyl, benzidolyl, phenanthrolinyl, acridinyl, phenanthridinyl, xanthenyl, and the like.

A heterocyclic group may be optionally substituted with one or more substituents, e.g., 1 to 5 substituents, at any available point of attachment. In addition to the substituents described under the definition of "substituted," other exemplary substituents include, but are not limited to, cycloalkyl or substituted cycloalkyl, cycloalkenyl or substituted cycloalkenyl, nitro, oxo (i.e., =O), cyano, alkyl or substituted alkyl, spiro-attached or fused cyclic substituents at any available point or points of attachment, spiro-attached cycloalkyl, spiro-attached cycloalkenyl, spiro-attached heterocycle (excluding heteroaryl), fused cycloalkyl, fused cycloalkenyl, fused heterocycle, fused aryl, and the like. The substituents can themselves be optionally substituted.

Unless otherwise indicated, any heteroatom with unsatisfied valences is assumed to have hydrogen atoms sufficient to satisfy the valences.

The term "substituted" means substituted by a below-described substituent group in any possible position. Substituent groups for the above moieties useful in this disclosure are those groups that do not significantly diminish the biological activity of the disclosed compound. Substituent groups that do not significantly diminish the biological activity of the disclosed compound include, but are not limited to, H, halogen, $N_3$, NCS, CN, $NO_2$, $NX_1X_2$, $OX_3$, $C(X_3)_3$, OAc, O-acyl, O-aroyl, NH-acyl, NH-aroyl, NHCOalkyl, CHO, C(halogen)$_3$, Ph, OPh, $CH_2Ph$, $OCH_2Ph$, $COOX_3$, $SO_3H$, $PO_3H_2$, $SO_2NX_1X_2$, $CONX_1X_2$, alkyl, alcohol, alkoxy, dioxolanyl, alkylmercapto, dithiolanyl, dithianyl, alkylamino, di-alkylamino, sulfonamide, thioalkoxy or methylene dioxy when the substituted structure has two adjacent carbon atoms, wherein $X_1$ and $X_2$ each independently comprise H or alkyl, and $X_3$ comprises H, alkyl, hydroxyloweralkyl. Unless otherwise specifically limited, a substituent group may be in any possible position.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body.

The phrase "pharmaceutically acceptable" is employed in this disclosure to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The terms "salt" or "salts", as employed in this disclosure, denote acidic and/or basic salts formed with inorganic and/or organic acids and bases.

The term "treating" with regard to a subject, refers to improving at least one symptom of the subject's disorder. Treating can be curing, improving, or at least partially ameliorating the disorder.

The term "disorder" is used in this disclosure to mean, and is used interchangeably with, the terms disease, condition, or illness, unless otherwise indicated.

The terms "effective amount" and "therapeutically effective amount" are used interchangeably in this disclosure and refer to an amount of a compound that, when administered to a subject, is capable of reducing a symptom of a disorder in a subject. The actual amount which comprises the "effective amount" or "therapeutically effective amount" will vary depending on a number of conditions including, but not limited to, the particular disorder being treated, the severity of the disorder, the size and health of the patient, and the route of administration. A skilled medical practitioner can readily determine the appropriate amount using methods known in the medical arts.

As used in this disclosure, the term "subject" includes, without limitation, a human or an animal. Exemplary animals include, but are not limited to, mammals such as mouse, rat, guinea pig, dog, cat, horse, cow, pig, monkey, chimpanzee, baboon, or rhesus monkey.

The terms "administer", "administering", or "administration" as used in this disclosure refer to either directly administering a compound or pharmaceutically acceptable salt of the compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a compound of Formula (I).

The terms "isolated" and "purified" as used in this disclosure refer to a component separated from other components of a reaction mixture or a natural source. In certain embodiments, the isolate contains at least about 50%, at least about 55%, at least about 60%, at least about 65%, at least about 70%, at least about 75%, at least about 80%, at least about 85%, at least about 90%, at least about 95%, or at least about 98% of the compound or pharmaceutically acceptable salt of the compound by weight of the isolate.

The term "tautomer" as used in this disclosure refers to compounds produced by the phenomenon wherein a proton of one atom of a molecule shifts to another atom. (March, *Advanced Organic Chemistry: Reactions, Mechanisms and Structures*, 4th Ed., John Wiley & Sons, pages 69-74 (1992)).

The following abbreviations are used in this disclosure and have the following definitions: DMF is dimethylformamide; DMSO is dimethylsulfoxide; Tris is tris(hydroxymethyl)aminomethane; "h" is hour or hours; and "RT" or "r.t." or "rt" is room temperature.

2. INHIBITORY COMPOUNDS

Inhibition of FAAH and/or MGL in a subject slows the normal degradation and inactivation of endogenous cannabinoid ligands by FAAH and/or MGL hydrolysis. This inhibition allows maintained or higher levels of those endogenous cannabinergic ligands to remain present in the subject. The maintained or higher levels of endocannabinoid ligands provide increased stimulation of the cannabinoid CB1 and CB2 receptors. The increased stimulation of the cannabinoid receptors allows the receptors to produce physiological effects at a maintained or increased level. Thus, a compound that inhibits the inactivation of endogenous cannabinoid ligands by FAAH and/or MGL increases the levels of endocannabinoids, thereby enhancing the activation of cannabinoid receptors. The compound may not directly modulate the cannabinoid receptors, but instead indirectly stimulates the cannabinoid receptors by increasing the in vivo levels of endocannabinoid ligands.

Certain chemical compounds have been found to inhibit the inactivation of cannabinergic ligands by FAAH and MGL. These compounds may not bind to, or may have lesser affinity for, the CB1 and/or CB2 cannabinoid receptors. Thus, the physiological action for such compounds may not be the direct modulation of the CB1 and/or CB1 receptors.

The inhibition of FAAH and/or MGL also enhances the effects of exogenous cannabinergic ligands and allows them to stimulate cannabinoid receptors at lower concentrations as compared to systems in which FAAH and/or MGL action is not inhibited. Thus, inhibition of FAAH and/or MGL also enhances the effects and duration of action of exogenous cannabinergic ligands.

Examples of cannabinergic ligands that bind to CB1 and/or CB2 include, but are not limited to, N-arachidonoyl ethanolamine (also known as anandamide or AEA) and 2-arachidonoylglycerol (2-AG) (both endogenous ligands for the cannabinoid CB1 and CB2 receptors), (−)-$\Delta^9$-tetrahydrocannabinol (the principal bioactive constituent of *cannabis* and exogenous ligand for the cannabinoid CB1 and CB2 receptors) and other synthetic cannabinergic analogs.

Marijuana-like cannabinoids, in addition to acting at cannabinoid receptors, also affect cellular membranes. These are known to cause undesirable side effects such as drowsiness, impairment of monoamide oxidase function, and impairment of non-receptor mediated brain function. Thus, the addictive and psychotropic properties of some cannabinoids limit their therapeutic value. Compounds that inhibit MGL activity provide an alternative mechanism for stimulating cannabinoid receptors and provide desirable pharmacological properties without the undesirable properties associated with increased concentrations of cannabinoids.

The present disclosure provides novel chemical compounds of Formula (I), R X Y, that inhibit FAAH or MGL or that jointly inhibit both FAAH and MGL, wherein Y is selected from the group consisting of:

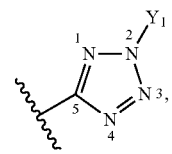

I 1

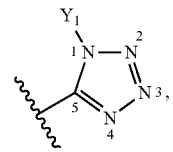

I 2

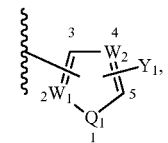

I 3

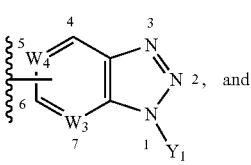

I 4 and

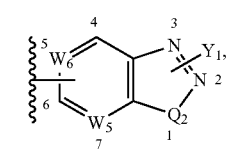

I 5 wherein:

$W_1$ is either CH or N if it is not bonded to X or $Y_1$, or $W_1$ is C if it is bonded to X or $Y_1$; if $W_1$ is N, then it can occupy position 2, 3, 4, or 5 in I 3;

$W_2$ is either CH or N if it is not bonded to X or $Y_1$, or $W_2$ is C if it is bonded to X or $Y_1$; if $W_2$ is N, then it can occupy position 2, 3, 4, or 5 in I 3;

$W_3$ is CH or N if it is not bonded to X, or $W_3$ is C if it is bonded to X; if $W_3$ is N then it can occupy position 4, 5, 6, or 7 in I 4;

$W_4$ is CH or N if it is not bonded to X, or $W_4$ is C if it is bonded to X; if $W_4$ is N then it can occupy position 4, 5, 6, or 7 in I 4;

$W_5$ is CH or N if it is not bonded to X, or $W_5$ is C if it is bonded to X; if $W_5$ is N then it can occupy position 4, 5, 6, or 7 in I 5;

$W_6$ is CH or N if it is not bonded to X, or $W_6$ is C if it is bonded to X; if $W_6$ is N then it can occupy position 4, 5, 6, or 7 in I 5;

$Q_1$ is $CH_2$, O, or NH if $Q_1$ is not bonded to X or $Y_1$, or $Q_1$ is CH or N if $Q_1$ is bonded to X or $Y_1$;

$Q_2$ is $CH_2$ or NH if $Q_2$ is not bonded to $Y_1$, or $Q_2$ is CH or N if $Q_2$ is bonded to $Y_1$;

$Y_1$ is selected from the group consisting of:

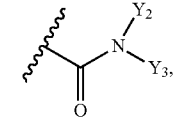
I 6

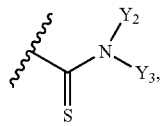
I 7

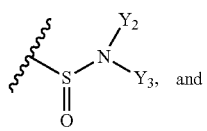
I 8, and

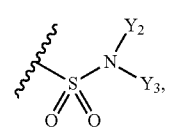
I 9 wherein:
$Y_2$ and $Y_3$ are each independently H, alkyl, cycloalkyl, aryl, heteroaryl, —$C_{1-5}$-alkyl-$Y_4$, -cycloalkyl-$Y_4$, -aryl-$Y_4$, or -heteroaryl-$Y_4$, or $Y_2$ and $Y_3$ together comprise part of a 5-7 membered saturated heterocyclic ring which can be substituted or unsubstituted and can contain up to one additional heteroatom selected from the group consisting of N, O, and S, with or without substitution on the heteroatom wherein the substituent is alkyl, aryl, heteroaryl, alkyl-aryl or alkyl-heteroaryl;

$Y_4$ is —F, —Cl, Br, —I, —OH, —SH, —$NH_2$, —CN, —$N_3$, —NCS, —$CONH_2$, —$CONR_{13}R_{14}$, —$SO_2NR_{13}R_{14}$, —COOH, —COOMe, —COOEt, $COCF_3$, —$NO_2$, —$CF_3$, —$SO_3H$, $SO_2R_{13}$, —P(O)(OH)$_2$, —PO(OR$_1$)$_2$, —C≡CH, or —CH=$CH_2$;

$R_{13}$ and $R_{14}$ are each independently H or $C_1$-$C_5$-alkyl;

X is —(CH$_2$)$_n$— or —(CH$_2$)$_j$-A-(CH$_2$)$_k$—, wherein:

A is —CH=CH—, —C=O, O, S, NH, —C(O)NH, —NHC=O, —NHC(O)NH—, OC(O)NH—, NHC(O)O, or —OC(O)O—;

n is an integer from 0 to 15;

j is an integer from 0 to 10;

k is an integer from 0 to 10;

and if n, j, or k is independently 0 the structural portion modified by that integer is absent and the adjacent subunits are directly connected;

wherein:

R is selected from the group consisting of:

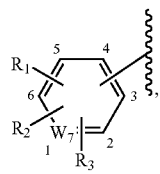
I 10

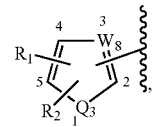
I 11

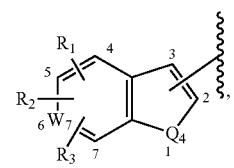
I 12

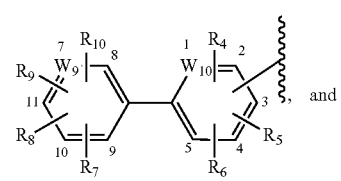
I 13, and

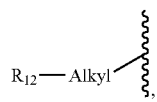
I 14 wherein:
$W_7$ is CH or N if $W_7$ is not bonded to X, $R_1$, $R_2$, or $R_3$, or $W_7$ is C if $W_7$ is bonded to X, $R_1$, $R_2$, or $R_3$; if $W_7$ is N then it can occupy position 1, 2, 3, 4, 5 or 6 in I 10 and 4, 5, 6 or 7 in I 12;

$W_8$ is CH or N if $W_8$ is not bonded to X, $R_1$, or $R_2$, or $W_8$ is C if $W_8$ is bonded to X, $R_1$, or $R_2$; if $W_8$ is N then it can occupy position 2, 3, 4 or 5 in I 11;

$W_9$ is CH or N if $W_9$ is not bonded to $R_7$, $R_8$, $R_9$, or $R_{10}$, or $W_9$ is C if $W_9$ is bonded to $R_7$, $R_8$, $R_9$, or $R_{10}$; if $W_9$ is N then it can occupy position 7, 8, 9, 10, or 11 in I 13;

$W_{10}$ is CH or N if $W_{10}$ is not bonded to X, $R_4$, $R_5$, or $R_6$, or $W_{10}$ is C if $W_{10}$ is bonded to X, $R_4$, $R_5$, or $R_6$; if $W_{10}$ is N then it can occupy position 1, 2, 3, 4, or 5 in I 13;

$Q_3$ is CH$_2$, O, S, or NH if $Q_3$ is not bonded to X, $R_1$, $R_2$, or $Q_3$ is CH or N if $Q_3$ is bonded to X, $R_1$, $R_2$;

$Q_4$ is CH$_2$, O, S, or NH if $Q_4$ is not bonded to X, or $Q_4$ is CH or N if $Q_4$ is bonded to X;

$R_1$, $R_2$, $R_3$, $R_4$, $R_5$, $R_6$, $R_7$, $R_8$, $R_9$, and $R_{10}$ are each independently —H, —F, —Cl, —Br, —I, —OH, —OAc, —SH, —$NH_2$, —CN, —$N_3$, —NCS, —$CONH_2$, —$SO_2NH_2$, —COOH, —$NO_2$, —CHO, —$CF_3$, —$OCF_3$, —$SO_3H$, —$SO_2F$, —O—P(O)(OH)$_2$, —O—P(O)(O-alkyl)$_2$, —O—P(O)(OH)(O-alkyl), —P(O)(O-alkyl)$_2$, —P(O)(OH)(O-alkyl), —Sn(alkyl)$_3$, —Si(alkyl)$_3$, —C≡CH, —CH=$CH_2$, -alkyl-$R_{12}$, or —Z-alkyl-$R_{12}$;

Z is —O—, —S—, —NH—, —C(O)—, —C(O)O—, —OC(O)—, —C(O)NH—, —NHC(O)—, —S(O)—, —S(O)$_2$—, —$SO_2NH$—, —$NHSO_2$—, —$SO_2O$—, or —$OSO_2$—;

$R_{12}$ is —H, —F, —Cl, —Br, —I, —OH, —OAc, —SH, —$NH_2$, —CN, —$N_3$, —NCS, —$CONH_2$, —$SO_2NH_2$, —COOH, —$NO_2$, —CHO, —$CF_3$, —$OCF_3$, —$SO_3H$, —$SO_2F$, —O—P(O)(OH)$_2$, —Sn(alkyl)$_3$, —Si(alkyl)$_3$, —OSi(alkyl)$_3$, —C≡CH, —$CH_2$—C≡CH and —CH=$CH_2$; and wherein if Y is I 1 or I 2 where $Y_1$ is —C(O)—N(CH$_3$)$_2$ and X is —(CH$_2$)$_n$— where n=1; then R can not be 1,1'-biphenyl-4-yl, 4-fluorophenyl, or 3-iodo-4-azidophenyl.

The compounds of Formula (I) can also form salts which are also within the scope of this disclosure. Reference to a compound of the present disclosure is understood to include reference to salts thereof, unless otherwise indicated. The compounds of Formula (I) may form pharmaceutically acceptable (i.e., non-toxic, physiologically acceptable) salts as well as other salts that are also useful, e.g., in isolation or purification steps which can be employed during preparation.

The compounds of Formula (I) which contain a basic moiety, such as, but not limited to, an amine or a pyridine or imidazole ring, can form salts with a variety of organic and inorganic acids. Exemplary acid addition salts include, but are not limited to, acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, hydroxyethanesulfonates (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (such as those formed with sulfuric acid), sulfonates, tartrates, thiocyanates, toluenesulfonates such as tosylates, undecanoates, and the like.

The compounds of Formula (I) which contain an acidic moiety, such as, but not limited to, a carboxylic acid, can form salts with a variety of organic and inorganic bases. Exemplary basic salts include, but are not limited to, ammonium salts, alkali metal salts such as sodium, lithium and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glycamides, t-butyl amines, and salts with amino acids such as arginine, lysine and the like. Basic nitrogen-containing groups can be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and the like.

The compounds of the present disclosure may have unnatural ratios of atomic isotopes at one or more of their atoms. For example, the compounds can be labeled with isotopes, such as deuterium, tritium, carbon-11, carbon-13, carbon-14, iodine-123, iodine-125 or fluorine-18. The present disclosure encompasses all isotopic variations of the described compounds, whether radioactive or not.

Exemplary nonlimiting compounds of Formula (I) are listed in Table 1 below. Solvates of the compounds of this disclosure, including hydrates of the compounds, as well as mixtures of the hydrate- and the keto-form of the compounds, are within the scope of this disclosure.

TABLE 1

| No. | Structure |
| --- | --- |
| 1a | 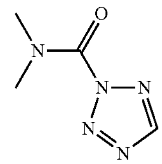 |
| 1b | 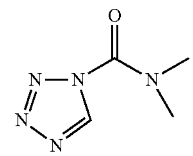 |
| 2 | 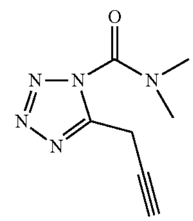 |
| 3a | 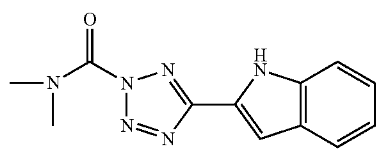 [SMILES: CN(C)C(=O)n1nnc(-c2cc3ccccc3[nH]2)n1] |
| 3b | 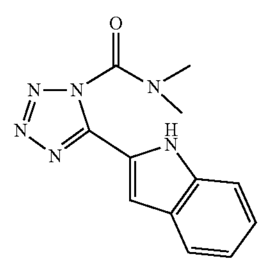 [SMILES: CN(C)C(=O)n1nnnc1-c1cc2ccccc2[nH]1] |
| 4 | 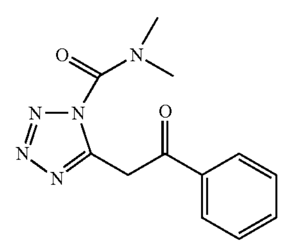 [SMILES: CN(C)C(=O)n1nnnc1CC(=O)c1ccccc1] |
| 5 | 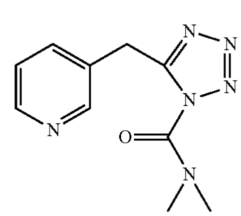 [SMILES: CN(C)C(=O)n1nnnc1Cc1cccnc1] |

TABLE 1-continued

| No. | Structure |
|---|---|
| 6* | (2,4-dichlorobenzyl)-tetrazole-N-carbonyl-morpholine |
| 7a | (2,4-dichlorobenzyl)-tetrazole-N-C(O)-N(CH₃)(phenyl) |
| 7b | (2,4-dichlorobenzyl)-tetrazole-N-C(O)-N(CH₃)(phenyl) (regioisomer) |
| 8a | (2,4-dichlorobenzyl)-tetrazole-N-C(O)-N(phenyl)₂ |
| 8b | (2,4-dichlorobenzyl)-tetrazole-N-C(O)-N(phenyl)₂ (regioisomer) |
| 9* | (2,4-dichlorobenzyl)-tetrazole-N-C(O)-N(ethyl)₂ |
| 10* | (2,4-dichlorobenzyl)-tetrazole-N-C(O)-N(isopropyl)₂ |
| 11* | (2,4-dichlorobenzyl)-tetrazole-N-C(O)-N(CH₃)(CH₂CH₂CH₂CH₂Cl) |
| 12* | (2,4-dichlorobenzyl)-tetrazole-N-C(O)-piperidine |
| 13* | (2,4-dichlorobenzyl)-tetrazole-N-C(O)-pyrrolidine |
| 14* | (2,4-dichlorobenzyl)-tetrazole-N-C(O)-(1,4-dioxa-8-azaspiro[4.5]decane) |
| 15* | (2,4-dichlorobenzyl)-tetrazole-N-C(O)-(4-benzylpiperazine) |
| 16a | (4-bromobenzyl)-tetrazole-N-C(O)-N(CH₃)₂ |
| 16b | (4-bromobenzyl)-tetrazole-N-C(O)-N(CH₃)₂ (regioisomer) |
| 17a | (2,4-dichlorobenzyl)-tetrazole-N-C(O)-N(CH₃)₂ |

TABLE 1-continued

| No. | Structure |
|---|---|
| 17b | 2,4-dichlorobenzyl-tetrazole-N,N-dimethylcarboxamide |
| 18a | 4-iodobenzyl-tetrazol-2-yl-N,N-dimethylcarboxamide |
| 18b | 4-iodobenzyl-tetrazol-1-yl-N,N-dimethylcarboxamide |
| 19a | 4-trifluoromethoxybenzyl-tetrazol-2-yl-N,N-dimethylcarboxamide |
| 19b | 4-trifluoromethoxybenzyl-tetrazol-1-yl-N,N-dimethylcarboxamide |
| 20a | 4-trifluoromethylbenzyl-tetrazol-2-yl-N,N-dimethylcarboxamide |
| 20b | 4-trifluoromethylbenzyl-tetrazol-1-yl-N,N-dimethylcarboxamide |
| 21a | 4-chlorobenzyl-tetrazol-2-yl-N,N-dimethylcarboxamide |
| 21b | 4-chlorobenzyl-tetrazol-1-yl-N,N-dimethylcarboxamide |
| 22a | 4-nitrobenzyl-tetrazol-2-yl-N,N-dimethylcarboxamide |
| 22b | 4-nitrobenzyl-tetrazol-1-yl-N,N-dimethylcarboxamide |
| 23a | 4-methylthiobenzyl-tetrazol-2-yl-N,N-dimethylcarboxamide |
| 23b | 4-methylthiobenzyl-tetrazol-1-yl-N,N-dimethylcarboxamide |
| 24a | 4-methoxybenzyl-tetrazol-2-yl-N,N-dimethylcarboxamide |
| 24b | 4-methoxybenzyl-tetrazol-1-yl-N,N-dimethylcarboxamide |
| 25a | 4-acetamidobenzyl-tetrazol-2-yl-N,N-dimethylcarboxamide |

TABLE 1-continued

| No. | Structure |
|---|---|
| 25b | 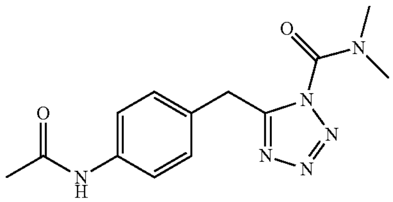 |
| 26a | 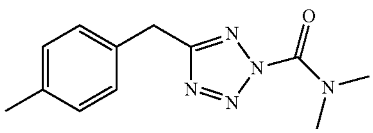 |
| 26b | 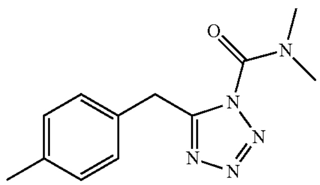 |
| 28 | 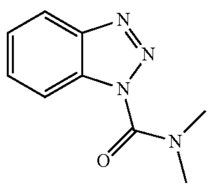 |
| 29 | 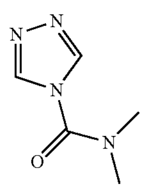 |
| 30 | 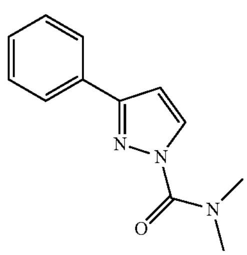 [SMILES: CN(C)C(=O)n1ccc(-c2ccccc2)n1] |
| 31 | 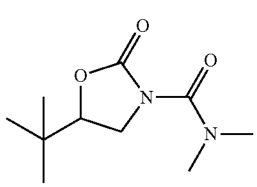 |
| 32 | 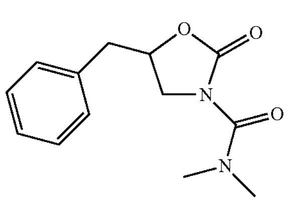 [SMILES: CN(C)C(=O)N1CC(Cc2ccccc2)OC1=O] |
| 33 | |
| 34 | |
| 35 | |
| 36a | |
| 36b | |
| 37 | |
| 38a | |

TABLE 1-continued

| No. | Structure |
|---|---|
| 38b | 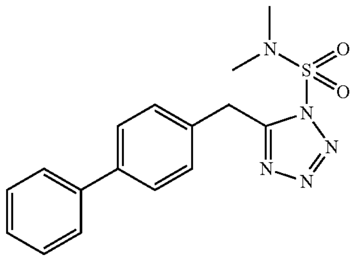 [SMILES: CN(C)S(=O)(=O)n1nnnc1Cc1ccc(-c2ccccc2)cc1] |
| 39 | 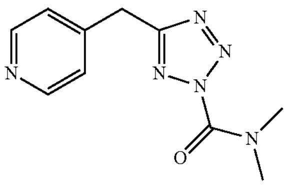 [SMILES: CN(C)C(=O)n1nnc(Cc2ccncc2)n1] |
| 40 | 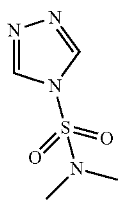 |
| 41 | 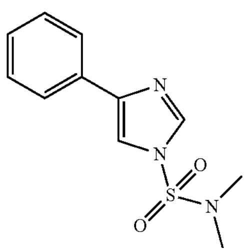 [SMILES: CN(C)S(=O)(=O)n1cnc(-c2ccccc2)c1] |
| 42 | 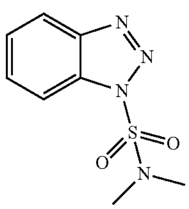 |
| 43 | 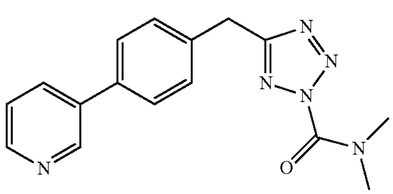 [SMILES: CN(C)C(=O)n1nnc(Cc2ccc(-c3cccnc3)cc2)n1] |
| 44 | 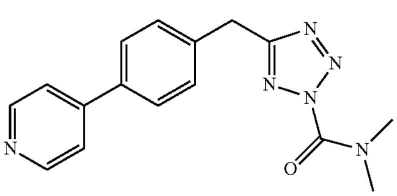 [SMILES: CN(C)C(=O)n1nnc(Cc2ccc(-c3ccncc3)cc2)n1] |
| 45 | |
| 46 | |
| 47 | |
| 48 | |
| 49 | |

TABLE 1-continued

| No. | Structure |
|---|---|
| 50 | 5-(naphthalen-1-ylmethyl)-N,N-dimethyl-2H-tetrazole-2-carboxamide |
| 51 | 5-(naphthalen-2-ylmethyl)-N,N-dimethyl-2H-tetrazole-2-carboxamide |
| 52 | 3-phenyl-N,N-dimethyl-1H-1,2,4-triazole-1-carboxamide |
| 53 | 3-phenyl-N-(4-chlorobutyl)-N-methyl-1H-1,2,4-triazole-1-carboxamide |
| 54 | 5-(pyridin-2-ylmethyl)-N,N-dimethyl-2H-tetrazole-2-carboxamide · HCl |
| 55 | 5-((4-(pyridin-4-yl)phenyl)methyl)-N,N-dimethyl-2H-tetrazole-2-carboxamide · HCl |
| 56 | 5-([1,1'-biphenyl]-2-ylmethyl)-N,N-dimethyl-2H-tetrazole-2-carboxamide |
| 57 | 5-([1,1'-biphenyl]-2-ylmethyl)-N,N-dimethyl-1H-tetrazole-1-carboxamide |
| 58 | N,N-dimethyl-1H-[1,2,3]triazolo[4,5-b]pyridine-1-carboxamide |
| 59 | 2-(benzyloxy)-N,N-dimethyl-7H-purine-7-carboxamide |
| 60 | N,N-dimethyl-7H-purine-7-carboxamide |
| 61 | N,N-dimethyl-1H-purine-1-carboxamide |

TABLE 1-continued

| No. | Structure |
|---|---|
| 62 | 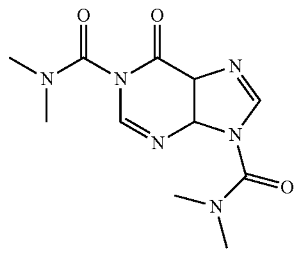 [SMILES: CN(C)C(=O)N1C=NC2C(N=CN2C(=O)N(C)C)C1=O] |
| 65 | 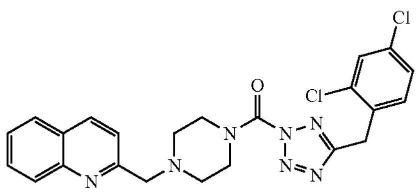 [SMILES: O=C(N1CCN(Cc2ccc3ccccc3n2)CC1)n1nnc(Cc2ccc(Cl)cc2Cl)n1] |
| 64 | 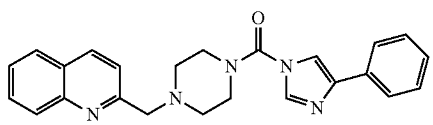 [SMILES: O=C(N1CCN(Cc2ccc3ccccc3n2)CC1)n1cnc(-c2ccccc2)c1] |
| 67 | 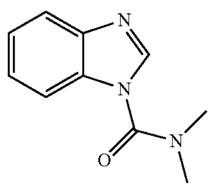 |
| 68 | 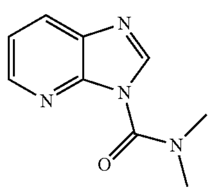 |
| 69 | 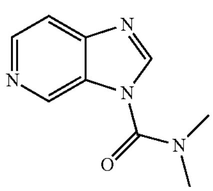 |
| 70* | 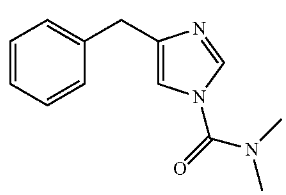 [SMILES: CN(C)C(=O)n1cnc(Cc2ccccc2)c1] |

*Mixture of isomers

The inhibitory compounds can be synthesized by chemical means as described in the Examples below. Novel compounds may be synthesized from commercially available starting material. The inhibitory compounds need not be made exclusively from the illustrative syntheses. A person of skill in the art understands that additional methods of making the inhibitory compounds exist. A person of skill in the art also understands that general synthetic schemes for the compounds disclosed herein can be understood from the illustrative schemes below.

The disclosed compounds, and pharmaceutically acceptable salts thereof, can be used to probe FAAH or MGL and related amidase or lipase mechanisms of catalysis, and to uncover the biological roles of lipid mediators such as anandamide, 2-arachidonoylglycerol and oleamide. For example, the disclosed compounds can be used as in vivo imaging agents; to maintain the level of anandamide or 2-arachidonoylglycerol in vitro; to study the effect of anandamide or 2-arachidonoylglycerol on cells and to enhance the levels of anandamide or 2-arachidonoylglycerol in vivo in order to study the effect of anandamide or 2-arachidonoylglycerol in animals and humans. The disclosed compounds can be used to characterize cells, for example, to determine if a cell type has cannabimimetic or amidase/lipase activity. For example, the disclosed compounds can be used to determine if a cell population expresses FAAH by treating the cells with a disclosed compound and then determining if there is an increase in the concentration of anandamide. Similarly, for example, the disclosed compounds can be used to determine if a cell population expresses MGL by treating the cells with a disclosed compound and then determining if there is an increase in the concentration of 2-arachidonoylglycerol.

The FAAH and MGL inhibitors disclosed herein can also be used as an aid in drug design, for example, as a control in assays for testing other compounds for their ability to inhibit FAAH and MGL, and to determine the structure activity requirements of FAAH and MGL inhibitors.

3. METHODS OF INHIBITION AND MODULATION

This disclosure is also directed to a method of modulating cannabinoid receptors in a biological sample by using the compounds of Formula (I), and pharmaceutically acceptable salts thereof. The method comprises (a) measuring the level of a cannabinergic ligand in the biological sample, (b) contacting the sample with a compound of Formula (I), thereby inhibiting an enzyme that hydrolyzes the cannabinergic ligand, and (c) measuring the level of the cannabinergic ligand in the contacted sample, the cannabinoid receptors being modulated if the level of the cannabinergic ligand in the contacted sample is the same or greater than the level of the cannabinergic ligand in the uncontacted sample.

In some instances, the enzyme inhibited is FAAH. Testing of some compounds of Formula (I) shows inhibition of FAAH in both in vitro and in vivo systems. Inhibition of FAAH has the effect of preventing the degradation of endocannabinoid ligands and increasing or maintaining the level of endocannabinoid ligands in a system. Thus, the disclosed compounds, when administered in a therapeutically effective amount, increase or maintain the in vivo concentration of endogenous cannabinergic ligands in a subject, thereby enhancing or maintaining activation of cannabinoid receptors. In other instances, the inhibitor inhibits MGL. The inhibition of MGL similarly prevents the degradation of endocannabinoid ligands and increasing or maintaining the level of endocannabinoid ligands in a system. Thus, the disclosed compounds, when administered in a therapeutically effective amount, increase or maintain the in vivo concentration of endogenous cannabinergic ligands in a subject, thereby enhancing or maintaining activation of cannabinoid receptors.

In still other cases, the inhibitory compounds inhibit FAAH and MGL. The joint inactivation of both enzymes leads to enhanced therapeutic benefits because cannabinoid receptors can be modulated by additional cannabinergic ligands.

Some analogs were tested for their FAAH/MGL inhibitory activity, which is expressed as % of inhibition (Tables 2, 3, and 4 below). The percentage of inhibition results from three-point assay (three concentrations of inhibitor are used) and it is less accurate (preliminary screening) than the $IC_{50}$/Ki values that are determined from eight-point assay (eight different concentrations of inhibitor were used). The percentage of inhibition describes the percentage by which the inhibitor reduces the velocity/rate of AAMCA (arachidonoyl-7-amino-4-methylcoumarin amide) or AHMMCE (arachidonoyl-7-hydroxy-6-methoxy-4-methylcoumarin ester) hydrolysis by FAAH or MGL respectively. The $IC_{50}$ is the concentration of the inhibitor, which results in 50% inhibition of the velocity/rate of AAMCA (arachidonoyl 7-amino-4-methylcoumarin amide) hydrolysis by FAAH or AHMMCE (Arachidonoyl, 7-hydroxy-6-methoxy-4-methylcoumarin ester) hydrolysis by MGL. The Ki value is the affinity constant and describes the ability of the compounds to inhibit the function of FAAH or MGL. The lower the $IC_{50}$/Ki values, the higher the affinity of the inhibitor for the enzyme and the higher its inhibitory activity. A detailed description of the methods used to test inhibitory activity of compounds is given below.

4. METHODS OF TREATMENT USING MGL INHIBITORY COMPOUNDS

As discussed above, the inhibitory compounds disclosed in this application inhibit FAAH and/or MGL in both in vitro and in vivo systems and prevent the degradation of endocannabinoid ligands, thus, enhancing or maintaining the level of endocannabinoid ligands in a system. The inhibitory compounds of this application, or a pharmaceutically acceptable salts thereof, are useful for administration in therapeutically effective amounts for enhancing or maintaining the in vivo concentration of endogenous cannabinergic ligands in a subject. The resulting enhanced or maintained modulation of the cannabinoid receptors by those cannabinergic ligands provides a variety of physiological effects.

A. Disorders

Some of the physiological effects provided by modulation of the cannabinoid receptors by cannabinergic ligands are useful to treat a disorder in a subject. Such treatable physiological effects include, but are not limited to, neuroprotection, reduction of inflammation, reduction of pain, reduction of central pain, reduction of peripheral pain, modulation of memory, sleep inducement, modulation of the immune system, hypotension, reduction of emesis, effects on gastrointestinal motility, effects on motor function, effects on intestinal transit and colonic propulsion, modulation of appetite, and modulation of fertility. Inhibition of FAAH and/or MGL activity increases or maintains the concentration of existing levels of endogenous cannabinergic ligands and thereby increases or maintains the magnitude and duration of the physiological effect provided by those cannabinergic ligands. Therefore, the disclosed compounds, and therapeutic formulations containing such compounds, enhance or maintain the magnitude and duration of the physiological effects produced by a cannabinergic ligand in a subject when administered in therapeutically effective amounts.

Disorders that can be treated by inhibition of FAAH or FAAH and/or MGL and indirect stimulation of the cannabinoid receptors include, for example, appetite disorders, metabolic disorders, movement disorders, inflammation, pain, neuropathic pain (e.g., neuropathic low back pain, complex regional pain syndrome, post trigeminal neuralgia, causalgia, toxic neuropathy, reflex sympathetic dystrophy, diabetic neuropathy, chronic neuropathy caused by chemotherapeutic agents), central pain, peripheral pain, neuropathy (e.g., diabetic neuropathy, pellagric neuropathy, alcoholic neuropathy, Beriberi neuropathy, burning feet syndrome), neurodegenerative diseases including multiple sclerosis, Parkinson's disease, Huntington's chorea, Alzheimer's disease, amyotrophic lateral sclerosis, memory disorders, mood disorders, sleep disorders, gastrointestinal motility disorders such as irritable bowel syndrome and diarrhea, cardiovascular disease, hypertension, dyslipidemia, atherosclerosis, osteoporosis, osteoarthritis, emesis, epilepsy, mental disorders such as schizophrenia and depression, glaucoma, cachexia, insomnia, traumatic brain injury, spinal cord injury, seizures, excitotoxin exposure, ischemia, AIDS wasting syndrome, psychological disorders including anxiety disorders (e.g., panic disorder, acute stress disorder, post-traumatic stress disorder, substance-induced anxiety disorders, obsessive-compulsive disorder, agoraphobia, specific phobia, social phobia), to modulate the immune system, to regulate fertility, to prevent or reduce diseases associated with motor function such as Tourette's syndrome, to provide neuroprotection, to produce peripheral vasodilation, to slow down intestinal transit and colonic propulsion, to treat several types of cancer, as well as other ailments in which a growing family of bioactive lipid mediators is implicated.

The disclosed inhibitory compounds and pharmaceutical formulations can also be used in combination with one or more agents treating and/or targeting the disorder or the endogenous cannabinergic system. Such agents include, but are not limited to, CB1 cannabinoid receptor agonists, CB2 cannabinoid receptor agonists, analgesics, anandamide transport inhibitors, COX-2 enzyme inhibitors, anxiolytics, antidepressants, and opioids. For example, these compounds and pharmaceutical formulations can be used in conjunction with other cannabinergic ligands that act directly on the CB1 and CB2 receptors.

In certain instances, the cannabinergic ligand is 2-arachidonoylglycerol. The disclosed compounds have high potential to be used as research tools to probe MGL and related lipase mechanisms of catalysis, and to uncover the biological roles of lipid mediators such as 2 arachidonoylglycerol. For example, the disclosed compounds can be used as in vivo imaging agents; to maintain the level of 2-arachidonoylglycerol in vitro to study the effect of 2-arachidonoylglycerol in cells and to enhance the levels of 2-arachidonoylglycerol in vivo in order to study the effect of 2-arachidonoylglycerol on humans and animals. The disclosed compounds can be used to characterize cells, for example, to determine if a cell type has cannabimimetic or lipase activity. For example, the disclosed compounds can be used to determine if a cell population expresses MGL by contacting the cells with a disclosed compound and then determining if there is an increase in the concentration of 2 arachidonoylglycerol. The inhibitors disclosed in this application can also be used as an aid in drug design, for example as a control in assays for testing other compounds for their ability to inhibit MGL and to determine the structure activity requirements of MGL inhibitors.

The disclosed compounds can also be used to prepare prodrugs. Prodrugs are known to those skilled in the art of pharmaceutical chemistry, and provide benefits such as increased adsorption and half-life. Those skilled in the art of drug delivery will readily appreciate that the pharmacokinetic properties of Formula (I) can be controlled by an appropriate choice of moieties to produce prodrug derivatives.

These compounds can also be used in conjunction with other cannabinergic ligands that act directly on the CB1 and CB2 receptors to enhance the ability of the other ligands to activate the CB1 and CB2 receptors.

B. Formulation

This disclosure is also directed to a pharmaceutical formulation comprising at least one compound of Formula (I), and a pharmaceutically-acceptable carrier. Such formulations are suitable for administration to a subject. The pharmaceutical formulation can be used for treating a disorder described above.

Any suitable pharmaceutically acceptable carrier known in the art can be used as long as it does not affect the inhibitory activity of a compound of Formula (I). Carriers may be used that efficiently solubilize the agents. Carriers include, but are not limited to, a solid, liquid, or a mixture of a solid and a liquid. The carriers can take the form of capsules, tablets, pills, powders, lozenges, suspensions, emulsions, or syrups. The carriers can include substances that act as flavoring agents, lubricants, solubilizers, suspending agents, binders, stabilizers, tablet disintegrating agents, and encapsulating materials. Other examples of suitable physiologically acceptable carriers are described in Remington's Pharmaceutical Sciences (21st ed. 2005), incorporated into this disclosure by reference.

Non-limiting examples of materials which can serve as pharmaceutically-acceptable carriers include: sugars, such as lactose, glucose, and sucrose; starches, such as corn starch and potato starch; cellulose and its derivatives, such as sodium carboxymethyl cellulose, ethyl cellulose, and cellulose acetate; powdered tragacanth; malt; gelatin; talc; excipients, such as cocoa butter and suppository waxes; oils, such as peanut oil, cottonseed oil, safflower oil, sesame oil, olive oil, corn oil, and soybean oil; glycols, such as propylene glycol; polyols, such as glycerin, sorbitol, mannitol, and polyethylene glycol; esters, such as ethyl oleate and ethyl laurate; agar; buffering agents, such as magnesium hydroxide and aluminum hydroxide; alginic acid; pyrogen-free water; isotonic saline, Ringer's solution, ethyl alcohol; phosphate buffer solutions; and other non-toxic compatible substances employed in pharmaceutical formulations.

The formulations can conveniently be presented in unit dosage form and can be prepared by any methods known in the art of pharmacy. The amount of compound of Formula (I) which can be combined with a carrier material to produce a single-dosage form will vary depending upon the subject being treated, the particular mode of administration, the particular condition being treated, among others. The amount of active ingredient that can be combined with a carrier material to produce a single-dosage form will generally be that amount of the compound that produces a therapeutic effect. Generally, out of one hundred percent, this amount will range from about 1% to about 99% of active ingredient, in some instances from about 5% to about 70%, in other instances from about 10% to about 30%.

Methods of preparing these formulations or compositions include the step of bringing into association a compound disclosed in this application with a carrier and, optionally, one or more accessory ingredients. In general, the formulations are prepared by uniformly and intimately bringing into association a compound of Formula (I) with liquid carriers, or timely divided solid carriers, or both, and then, if necessary, shaping the product.

In solid dosage forms of the disclosed compounds for oral administration (e.g., capsules, tablets, pills, dragees, powders, granules, and the like), the active ingredient is mixed with one or more additional ingredients, such as sodium citrate or dicalcium phosphate, and/or any of the following: fillers or extenders, such as, but not limited to, starches, lactose, sucrose, glucose, mannitol, and/or silicic acid; binders, such as, but not limited to, carboxymethylcellulose, alginates, gelatin, polyvinyl pyrrolidone, sucrose, and/or acacia; humectants, such as, but not limited to, glycerol; disintegrating agents, such as, but not limited to, agar, calcium carbonate, potato or tapioca starch, alginic acid, certain silicates, and sodium carbonate; solution retarding agents, such as, but not limited to, paraffin; absorption accelerators, such as, but not limited to, quaternary ammonium compounds; wetting agents, such as, but not limited to, cetyl alcohol and glycerol monostearate; absorbents, such as, but not limited to, kaolin and bentonite clay; lubricants, such as, but not limited to, talc, calcium stearate, magnesium stearate, solid polyethylene glycols, sodium lauryl sulfate, and mixtures thereof; and coloring agents. In the case of capsules, tablets, and pills, the pharmaceutical compositions can also comprise buffering agents. Solid compositions of a similar type can also be employed as fillers in soft and hard-filled gelatin capsules using such excipients as lactose or milk sugars, as well as high molecular weight polyethylene glycols, and the like.

In powders, the carrier is a finely-divided solid, which is mixed with an effective amount of a finely-divided agent. Powders and sprays can contain, in addition to a compound of Formula (I), excipients, such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Tablets for systemic oral administration can include one or more excipients as known in the art, such as, for example, calcium carbonate, sodium carbonate, sugars (e.g., lactose, sucrose, mannitol, sorbitol), celluloses (e.g., methyl cellulose, sodium carboxymethyl cellulose), gums (e.g., arabic, tragacanth), together with one or more disintegrating agents (e.g., maize, starch, or alginic acid, binding agents, such as, for example, gelatin, collagen, or acacia), lubricating agents (e.g., magnesium stearate, stearic acid, or talc), inert diluents, preservatives, disintegrants (e.g., sodium starch glycolate), surface-active and/or dispersing agent. A tablet can be made by compression or molding, optionally with one or more accessory ingredients.

In solutions, suspensions, emulsions or syrups, an effective amount of a disclosed compound is dissolved or suspended in a carrier, such as sterile water or an organic solvent, such as aqueous propylene glycol. Other compositions can be made by dispersing the agent in an aqueous starch or sodium carboxymethyl cellulose solution or a suitable oil known to the art. The liquid dosage forms can contain inert diluents commonly used in the art, such as, for example, water or other solvents, solubilizing agents and emulsifiers, such as, but not limited to, ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols, and fatty acid esters of sorbitan, and mixtures thereof.

Besides inert diluents, the oral compositions can also include adjuvants, such as wetting agents, emulsifying and suspending agents, sweetening, flavoring, coloring, perfuming, and preservative agents.

Suspensions can contain, in addition to the active compound, suspending agents as, for example, ethoxylated isostearyl alcohols, polyoxyethylene sorbitol and sorbitan esters, microcrystalline cellulose, aluminum metahydroxide, bentonite, agar and tragacanth, and mixtures thereof.

Formulations of the pharmaceutical compositions for rectal or vaginal administration can be presented as a suppository, which can be prepared by mixing one or more compounds of this disclosure with one or more suitable non-irritating excipients or carriers comprising, for example, cocoa butter, polyethylene glycol, a suppository wax or a salicylate, and which is solid at RT but liquid at body temperature and, thus, will melt in the rectum or vaginal cavity and release the agents. Formulations suitable for vaginal administration also include, but are not limited to, pessaries, tampons, creams, gels, pastes, foams, or spray formulations containing such carriers as are known in the art to be appropriate.

Dosage forms for the topical or transdermal administration of a compound of this disclosure include, but are not limited to, powders, sprays, ointments, pastes, creams, lotions, gels, solutions, patches, and inhalants. The active compound can be mixed under sterile conditions with a pharmaceutically-acceptable carrier, and with any preservatives, buffers, or propellants.

Ointments, pastes, creams, and gels can contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Transdermal patches have the added advantage of providing controlled delivery of a compound of Formula (I) to the body. Such dosage forms can be made by dissolving or dispersing the agents in the proper medium. Absorption enhancers can also be used to increase the flux of the agents across the skin. The rate of such flux can be controlled by either providing a rate controlling membrane or dispersing the compound in a polymer matrix or gel.

The compounds of Formula (I) are administered in a therapeutically effective amount to a patient in need of such treatment. Such an amount is effective in treating a disorder of the patient. This amount can vary, depending on the activity of the agent utilized, the nature of the disorder, and the health of the patient. A skilled practitioner will appreciate that the therapeutically-effective amount of a compound of Formula (I) can be lowered or increased by fine-tuning and/or by administering more than one compound of Formula (I), or by administering a compound of Formula (I) together with a second agent (e.g., antibiotics, antifungals, antivirals, NSAIDS, DMARDS, steroids, etc.). Therapeutically-effective amounts can be easily determined, for example, empirically by starting at relatively low amounts and by step-wise increments with concurrent evaluation of beneficial effect (e.g., reduction in symptoms). The actual effective amount will be established by dose/response assays using methods standard in the art (Johnson et al., Diabetes., (1993) 42:1179). As is known to those in the art, the effective amount will depend on bioavailability, bioactivity, and biodegradability of the compound of Formula (I).

A therapeutically-effective amount is an amount that is capable of reducing a symptom of a disorder in a subject. Accordingly, the amount will vary with the subject being treated. Administration of the compound of Formula (I) can be hourly, daily, weekly, monthly, yearly, or a single event. For example, the effective amount of the compound can comprise from about 1 µg/kg body weight to about 100 mg/kg body weight. In one embodiment, the effective amount of the compound comprises from about 1 µg/kg body weight to about 50 mg/kg body weight. In a further embodiment, the effective amount of the compound comprises from about 10 µg/kg body weight to about 10 mg/kg body weight. When one or more compounds of Formula (I) or agents are combined with a carrier, they can be present in an amount of about 1 weight percent to about 99 weight percent, the remainder being composed of the pharmaceutically-acceptable carrier.

C. Administration

Methods of administration of the therapeutic formulations comprising the compounds of Formula (I) can be by any of a number of methods known in the art. These methods include, but are not limited to, local or systemic administration. Exemplary routes of administration include, but are not limited to, oral, parenteral, transdermal, intradermal, intramuscular, intraperitoneal, intravenous, subcutaneous, intranasal (e.g., nebulizer, inhaler, aerosol dispenser), colorectal, rectal, intravaginal, and any combinations thereof. In addition, it may be desirable to introduce pharmaceutical compositions of the disclosed compounds into the central nervous system by any suitable route, including intraventricular and intrathecal injection. Intraventricular injection can be facilitated by an intraventricular catheter, for example, attached to a reservoir, such as an Ommaya reservoir. Methods of introduction can be provided by rechargeable or biodegradable devices, e.g., depots. Furthermore, administration can occur by coating a device, implant, stent, or prosthetic. The compounds of Formula (I) can also be used to coat catheters in any situation where catheters are inserted in the body.

The therapeutic formulations containing a compound of Formula (I) can also be administered as part of a combinatorial therapy with other agents. Combination therapy refers to any form of administration combining two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either simultaneously or sequentially. Thus, an individual who receives such treatment can have a combined (conjoint) effect of different therapeutic compounds.

In other instances, for example, in the case of inflammatory conditions, a therapeutic formulation containing a compound of Formula (I) can be administered in combination with one or more other agents useful in the treatment of inflammatory diseases or conditions. Agents useful in the treatment of inflammatory diseases or conditions include, but are not limited to, anti-inflammatory agents, or antiphlogistics. Exemplary antiphlogistics include, but are not limited to, glucocorticoids, such as cortisone, hydrocortisone, prednisone, prednisolone, fluorcortolone, triamcinolone, methylprednisolone, prednylidene, paramethasone, dexamethasone, betamethasone, beclomethasone, fluprednylidene, desoxymethasone, fluocinolone, flunethasone, diflucortolone, clocortolone, clobetasol and fluocortin butyl ester; immunosuppressive agents such as anti-TNF agents (e.g., etanercept, infliximab) and IL-1 inhibitors; penicillamine; non-steroidal anti-inflammatory drugs (NSAIDs) which encompass anti-inflammatory, analgesic, and antipyretic drugs such as salicyclic acid, celecoxib, difunisal and from substituted phenylacetic acid salts or 2-phenylpropionic acid salts, such as alclofenac, ibutenac, ibuprofen, clindanac, fenclorac, ketoprofen, fenoprofen, indoprofen, fenclofenac, diclofenac, flurbiprofen, piprofen, naproxen, benoxaprofen, carprofen and cicloprofen; oxican derivatives, such as piroxican; anthranilic acid derivatives, such as mefenamic acid, flufenamic acid, tolfenamic acid and meclofenamic acid, anilino-substituted nicotinic acid derivatives, such as the fenamates miflumic acid, clonixin and flunixin; heteroarylacetic acids wherein heteroaryl is a 2-indol-3-yl or pyrrol-2-yl group, such as indomethacin, oxmetacin, intrazol, acemetazin, cinmetacin, zomepirac, tolmetin, colpirac and tiaprofenic acid; idenylacetic acid of the sulindac type; analgesically active heteroaryloxyacetic acids, such as benzadac; phenylbutazone; etodolac; nabunetone; and disease modifying antirheumatic drugs (DMARDs) such as methotrexate, gold salts, hydroxychloroquine, sulfasalazine, ciclosporin, azathioprine, and leflunomide. Other therapeutics useful in the treatment of inflammatory diseases or conditions include antioxidants. Antioxidants can be natural or synthetic. Antioxidants are, for example, superoxide dismutase (SOD), 21 aminosteroids/aminochromans, vitamin C or E, etc. Many other antioxidants are known to those of skill in the art. The compounds of Formula (I) can serve as part of a treatment regimen for an inflammatory condition, which may combine many different anti-inflammatory agents. For example, the subject compounds can be administered in combination with one or more of an NSAID, DMARD, or immunosuppressant. The subject compounds can also be administered in combination with methotrexate. The subject antibodies can also be administered in combination with a TNF-α inhibitor.

In the case of cardiovascular disease conditions, and particularly those arising from atherosclerotic plaques, which are thought to have a substantial inflammatory component, the therapeutic formulation including a compound of Formula (I) can be administered in combination with one or more other agents useful in the treatment of cardiovascular diseases. Agents useful in the treatment of cardiovascular diseases include, but are not limited to, β-blockers such as carvedilol, metoprolol, bucindolol, bisoprolol, atenolol, propranolol, nadolol, timolol, pindolol, and labetalol; antiplatelet agents such as aspirin and ticlopidine; inhibitors of angiotensin-converting enzyme (ACE) such as captopril, enalapril, lisinopril, benazopril, fosinopril, quinapril, ramipril, spirapril, and moexipril; and lipid-lowering agents such as mevastatin, lovastatin, simvastatin, pravastatin, fluvastatin, atorvastatin, and rosuvastatin.

In the case of cancer, the subject compounds can be administered in combination with one or more anti-angiogenic factors, chemotherapeutics, or as an adjuvant to radiotherapy. It is further envisioned that the administration of the subject compounds will serve as part of a cancer treatment regimen, which may combine many different cancer therapeutic agents.

5. A NOVEL FLUOROGENIC SUBSTRATE

As discussed above, FAAH and MGL hydrolyze certain endogenous and exogenous cannabinergic ligands. This application provides a novel substrate that fluoresces when hydrolyzed by MGL, wherein the substrate is a compound of the formula:

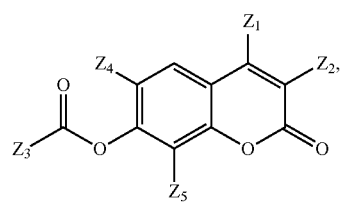

wherein $Z_1$ and $Z_2$ are each independently H, alkyl, cycloalkyl, aryl, or heteroaryl, or $Z_1$ and $Z_2$ together comprise part of a 5 or 6 membered saturated heterocyclic ring. $Z_3$ is alkyl, aryl, or —$(CH_2)_n$—$(CH=CH)_m$—$(CH_2)_o$—$(CH=CH)_p$—$(CH_2)_q$—$CH_3$, wherein n, m, o, p, q=0-6. $Z_3$ is selected from essential and non-essential fatty acid alkyl chain. $Z_4$ and $Z_5$ are each independently H, alkyl, aryl, —O-alkyl, or —NH-alkyl.

In some instances, the novel fluorogenic substrate is arachidonyl-7-hydroxy-6-methoxy-4-methyl-coumarin ester.

This application also provides a method of evaluating the activity of a monoacylglycerol lipase using the above substrate. The method comprises the first steps of: adding a sample containing a monoacylglycerol lipase, with the fluorogenic substrate of the formula:

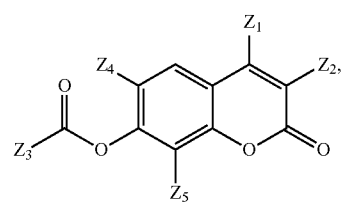

wherein $Z_1$ and $Z_2$ are each independently H, alkyl, cycloalkyl, aryl, or heteroaryl, or $Z_1$ and $Z_2$ together comprise part of a 5 or 6 membered saturated heterocyclic ring. $Z_3$ is alkyl, aryl, or —$(CH_2)_n$—$(CH=CH)_m$—$(CH_2)_o$—$(CH=CH)_p$—$(CH_2)_q$—$CH_3$, wherein n, m, o, p, q=0-6. $Z_3$ is selected from essential and non-essential fatty acid alkyl chain. $Z_4$ and $Z_5$ are each independently H, alkyl, aryl, —O-alkyl, or —NH-alkyl.

Next, the assay mixture is incubated for about 30 to about 180 min under conditions to allow the MGL to hydrolyze the fluorogenic substrate, thereby producing a fluorescent product. Finally, an amount of fluorophore or fluorescent hydrolysis product formed is detected. The amount of fluorophore or fluorescent hydrolysis product formed is indicative of the monoacylglycerol lipase activity of the sample.

In some instances, the novel fluorogenic substrate is arachidonyl-7-hydroxy-6-methoxy-4-methyl-coumarin ester.

In some instances, the sample is a biological sample. The biological sample can be in vivo or in vitro. In particular instances, the biological sample comprises cells. In certain instances, the biological sample comprises the cells of a subject. In further instances, the biological sample comprises biological membranes, lipid bilayers, or micelles.

This application also provides a method of identifying a compound capable of inhibiting monoacylglycerol lipase activity. The method comprises the steps of: adding a sample containing a monoacylglycerol lipase, with a test compound; incubating the mixture for a sufficient period of time to all the MGL to bind with the compound (about 30 to about 180 min). Next added to the mixture is a fluorogenic substrate of the formula:

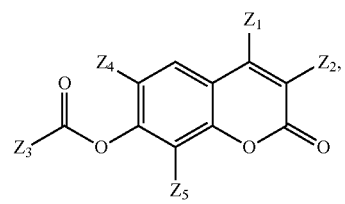

wherein $Z_1$ and $Z_2$ are each independently H, alkyl, cycloalkyl, aryl, or heteroaryl, or $Z_1$ and $Z_2$ together comprise part of a 5 or 6 membered saturated heterocyclic ring. $Z_3$ is alkyl, aryl, or —$(CH_2)_n$—$(CH=CH)_m$—$(CH_2)_o$—$(CH=CH)_p$—$(CH_2)_q$—$CH_3$, wherein n, m, o, p, q=0-6. $Z_3$ is selected from essential and non-essential fatty acid alkyl chain. $Z_4$ and $Z_5$ are each independently H, alkyl, aryl, —O-alkyl, or —NH-alkyl.

The mixture is then incubated for about 30 min to about 180 min under conditions to allow the free MGL to hydrolyze the fluorogenic substrate, thereby producing a fluorescent product. The amount of fluorophore or fluorescent hydrolysis product formed is detected. The amount of fluorophore or fluorescent hydrolysis product formed is indicative of the monoacylglycerol lipase activity. Finally, the amount of fluorophore or fluorescent hydrolysis product formed is compared to the amount of fluorophore or fluorescent hydrolysis product formed in a control assay incubated in the absence of the test compound. If the amount of fluorophore or fluorescent hydrolysis product formed is detectably less in the first sample with the test compound, then the test compound is an inhibitor of MGL activity.

In some instances, the assay can be performed as described below in the Examples section using arachidonyl-7-hydroxy-6-methoxy-4-methyl-coumarin ester.

In some instances, the determining step is performed by measurement of fluorescence energy. In certain other instances, the method is conducted in a multiwell plate. The method can comprise a portion of a high throughput screening program. The method can be conducted in conjunction with a drug discovery effort. In some instances, the monoacylglycerol lipase is a mammalian monoacylglycerol lipase. In other instances, the monoacylglycerol lipase is a rodent, murine, rat, mouse, or human monoacylglycerol lipase.

The disclosure is further illustrated by the following examples, which are not to be construed as limiting this disclosure in scope or spirit to the specific procedures described in this disclosure. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

EXAMPLES

Testing of Inhibitory Compounds

1. Vector Construction

A full-length cDNA clone of the human MGL transcript variant 1 (gi: 51242951) was obtained from OriGene Technologies (Rockville, Md.). The coding part of the MGL sequence (except the translation initiation codon ATG) was amplified by a polymerase chain reaction (PCR) using forward AACACGTGCCAGAGGAAAGTTCCC and reverse AAGAGCTCAGGGTGGGGACGCAG primers containing PmlI and SacI restriction enzyme recognition sites, respectively. iProof high-fidelity DNA polymerase (Bio-Rad, Hercules, Calif.) was used in the PCR amplification with 33 cycles, each consisting of denaturation at 94° C. for 10 s, annealing at 55° C. for 33 s, and extension at 72° C. for 1 min. The PCR product and pET45b vector were digested with PmlI and SacI restriction enzymes, and the vector was dephosphorylated with CIP followed by in-gel purification using the MinElute Gel Extraction Kit (Qiagen Corp., Valencia, Calif.). The fragment was inserted into the vector directly downstream after the 6 histidine and valine codons, generating the construct pET45His6hMGL for expression of hMGL containing an N-terminal His6-tag. GC10 E. coli cells were used for DNA transformation and plasmid propagation. Mini- and midi-scale plasmid DNA preparations were performed using a GenElute Plasmid Miniprep Kit (Sigma) and PureYield Plasmid Midiprep System (Promega, Madison, Wis.), respectively. In-frame vector-fragment junctions and the coding sequence of the recombinant gene were confirmed by sequencing. The pET45His6hMGL construct was transformed into BL21 (DE3) and Origami (DE3) E. coli expression strains (Novagen, Madison, Wis.).

2. Analytical Screening for hMGL Expression

Multiple E. coli colonies containing pET45His6hMGL plasmid were inoculated into 2 mL of Luria broth (Sigma) supplemented with ampicillin (100 µg/mL) and grown overnight at 37° C. with shaking (250 rpm). The next morning, 0.2 mL of this culture was innoculated into 20 mL fresh Luria broth-ampicillin medium and incubated under the same conditions. When culture turbidity reached an $OD_{600}$ of 0.5-0.7, expression from the T7 promoter was induced by adding isopropyl-β-D-thio-galactopyranoside (1 mM) (Sigma). At each h during the first 6 h of induction and, finally, at 19 h post-induction, a 1 mL culture sample was collected. Cells were harvested by centrifugation at 5,000 g for 10 min at 4° C. and washed with phosphate-buffered saline (PBS). Soluble and inclusion-body subfractions were prepared and their proteins isolated using B-PER Bacterial Protein Extraction Reagent (Pierce, Rockford, Ill.).

In brief, E. coli cells (5-10 mg) were collected from 1 mL of culture by centrifugation at 7,000 g for 5 min and resuspended in 150 µL B-PER reagent. The suspension was centrifuged at 15,000 g for 5 min, and the supernatant containing soluble protein was recovered. The resulting pellet was resuspended in 150 µL B-PER reagent followed by addition of 3 µL lysozyme solution (10 µg/µL) (Sigma) and 500 µL 1:10-diluted B-PER reagent. Inclusion bodies were collected by centrifugation at 15,000 g for 10 min. Fractions were processed for evaluation of hMGL expression over time by SDS-PAGE and immunodetection (below).

3. Preparative hMGL Purification

A single E. coli BL21 (DE3) colony containing the pET45His6hMGL plasmid was inoculated into 12 mL of Luria broth-ampicillin medium and grown overnight with shaking (250 rpm) at 37° C. The next morning, 10 mL of this culture was inoculated into 1 L of fresh Luria broth-ampicillin and allowed to grow until culture turbidity reached an $(OD)_{600}$ of 0.6-0.8, at which time expression from the T7 promoter was induced by adding isopropyl-β-D-thio-galactopyranoside (1 mM). After 5 h induction, the cells were harvested by centrifugation at 5,000 g for 10 min at 4° C., washed with PBS, and held at −80° C. Five grams (wet-weight) of cells were resuspended in 50 mL lysis buffer (100 mM NaCl; 50 mM Tris, pH 8.0) supplemented with Triton X-100 (0.5%), lysozyme (0.2 mg/mL), and DNase I (25 µg/ml) and disrupted on ice by three, one-min sonication cycles, each consisting of 1-sec sonication bursts at 50 W power separated from each other by a 2-sec interval (Vibra-Cell 500 W, Sonics, Newtown, Conn.). The cell lysate was centrifuged at 10,000 g for 30 min at 4° C. To isolate hMGL by immobilized metal affinity chromatography (IMAC), the supernatant was incubated with 0.5 mL (bed volume) pre-equilibrated BD Talon™ metal-affinity resin (Clontech, Mountain View, Calif.) for 1 h at RT with gentle agitation. The suspension was then transferred to a gravity-flow column and allowed to settle. The resin was washed with 15 mL lysis buffer, then 15 mL lysis buffer containing 0.5% Triton X-100 and 10 mM imidazole. His6-tagged protein was eluted with 4 mL lysis buffer containing 0.1% Triton X-100 and 200 mM imidazole and analyzed by SDS-PAGE.

4. Fluorescent Enzyme Assay

The enzyme (FAAH and MGL) assays were performed in 96 well plates (Coster #3650) in a total volume of 200 uL. Fluorogenic substrate AAMCA (arachidonoyl 7-amino-4-methylcoumarin amide) for FAAH and AHMMCE (arachidonoyl 7-hydroxy-6-methoxy-4-methylcoumarin ester) for MGL were used using BioTek Synergy HT Microplate Reader. Compounds and substrates were dissolved in DMSO provide a 10 mM stock solution and kept as a stock solution at −20° C. until used for assay. Stock solutions were thawed and reconstituted in 50:50 DMSO/assay buffer to a final DMSO concentration per well below 8%. This ensures that the compounds and substrate are in solution during assay. For the screening assay, we used 3 concentrations of 1/10/100 uM of test compounds or 15 ug of ΔTM rFAAH (cell lysate obtained by recombinant procedure) in 50 mM TME-0.1% BSA buffer at pH=7.4 and 175 ng of hMGL (cell lysate obtained by recombinant procedure or purified MGL enzyme) in 50 mM Tris pH=7.4 and incubated for 15 min at 25° C. Appropriate substrate was added to adjust the final concentration in each well to 20 uM for FAAH (2× Km) and 10 uM for MGL (1×KM). Fluorescence readings were performed at $\lambda ex=360/\lambda em=460$ for 4 h using Kinetic assay protocol at every 20 min (the fluorescent product coumarin produced is quantitated by this procedure). The readings at 3 h for FAAH and 2 h for MGL (linear maximum hydrolysis kinetics of enzyme on substrate) were used to calculate percent inhibition based on controls. Compounds which had more than 50 percent inhibition at 10 uM were selected for dose response study to determine $IC_{50}$ values. The dose response at 8 concentration points was performed as with the screening assay except that compounds were serially diluted to 8 concentration points which were chosen based on $IC_{50}$ value, which were calculated from the screening assay results. Assays are run twice in triplicates and Graphpad Prism software is used to plot inhibition data to obtain $IC_{50}$ values.

5. Results

Some synthesized and purified FAAH and MGL inhibitors of compound Formula (I) and their ability to inhibit MGL and FAAH at 10 nM and 1000 nM are depicted in Tables 2, 3, and 4, below.

TABLE 2

| | | % Inhibition of Enzyme by inhibitor at 10 nM and 1000 nM | | | |
| | | MGL | | FAAH | |
| Number | Structure | 10 nM | 1000 nM | 10 nM | 1000 nM |
| --- | --- | --- | --- | --- | --- |
| 1a | | 58 | 73 | | |
| 1b | | 13 | 51 | | |
| 2 | | | | 35 | 90 |
| 3a | | | | 9 | 93 |

TABLE 2-continued

| Number | Structure | % Inhibition of Enzyme by inhibitor at 10 nM and 1000 nM | | | |
|---|---|---|---|---|---|
| | | MGL | | FAAH | |
| | | 10 nM | 1000 nM | 10 nM | 1000 nM |
| 3b | | 92 | | 97 | |
| 4 | | 90 | | 100 | |
| 5 | | 81 | | 84 | |
| 6* | | 88 | | 94 | |
| 7a | | 58 | | 84 | |
| 7b | | 8 | | 89 | |

TABLE 2-continued

| | | % Inhibition of Enzyme by inhibitor at 10 nM and 1000 nM | | | |
|---|---|---|---|---|---|
| | | MGL | | FAAH | |
| Number | Structure | 10 nM | 1000 nM | 10 nM | 1000 nM |
| 8a | | | 100 IC$_{50}$ = 40 nM | | 66 IC$_{50}$ = 1300 nM |
| 8b | | | 21 | | 9 |
| 9* | | | 43 | | 95 |
| 10* | | | 11 | | 94 |
| 11* | | | 98 | | 100 |
| 12* | | | 98 | | 100 |

TABLE 2-continued

| | | % Inhibition of Enzyme by inhibitor at 10 nM and 1000 nM | | | |
| | | MGL | | FAAH | |
| Number | Structure | 10 nM | 1000 nM | 10 nM | 1000 nM |
| --- | --- | --- | --- | --- | --- |
| 13* | (2,4-dichlorobenzyl-tetrazole-N-C(O)-pyrrolidine) | 93 | | 97 | |
| 14* | (2,4-dichlorobenzyl-tetrazole-N-C(O)-piperidine-4-spiro-1,3-dioxolane) | | 52 | | 97 |
| 15* | (2,4-dichlorobenzyl-tetrazole-N-C(O)-4-benzylpiperazine) | | 63 | | 95 |
| 16a | (4-bromobenzyl-tetrazole-N-C(O)-N(CH₃)₂) | 98 | | 92 | |
| 16b | (4-bromobenzyl-tetrazole-N-C(O)-N(CH₃)₂ isomer) | 64 | | 92 | |
| 17a | (2,4-dichlorobenzyl-tetrazole-N-C(O)-N(CH₃)₂) | 99 | | 93 | |
| 17b | (2,4-dichlorobenzyl-tetrazole-N-C(O)-N(CH₃)₂ isomer) | 97 | | 86 | |
| 18a | (4-iodobenzyl-tetrazole-N-C(O)-N(CH₃)₂) | 97 | | 92 | |

TABLE 2-continued
| Number | Structure | % Inhibition of Enzyme by inhibitor at 10 nM and 1000 nM | | | |
|---|---|---|---|---|---|
| | | MGL | | FAAH | |
| | | 10 nM | 1000 nM | 10 nM | 1000 nM |
| 18b | 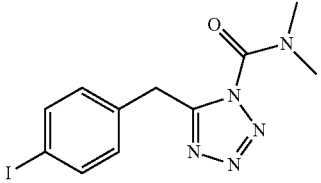 [SMILES: CN(C)C(=O)n1nnnc1Cc1ccc(I)cc1] | 64 | | 86 | |
| 19a | 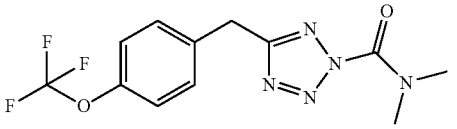 [SMILES: CN(C)C(=O)n1nnc(Cc2ccc(OC(F)(F)F)cc2)n1] | 99 | | 92 | |
| 19b | 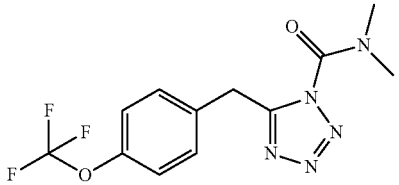 [SMILES: CN(C)C(=O)n1nnnc1Cc1ccc(OC(F)(F)F)cc1] | 76 | | 91 | |
| 20a | 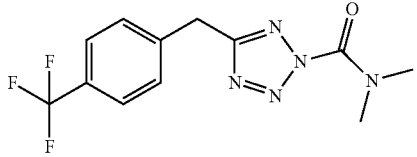 [SMILES: CN(C)C(=O)n1nnc(Cc2ccc(C(F)(F)F)cc2)n1] | 98 | | 93 | |
| 20b | 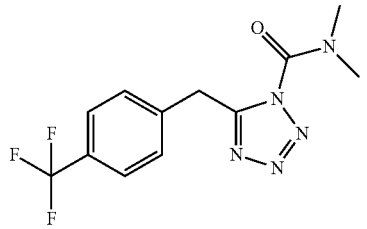 [SMILES: CN(C)C(=O)n1nnnc1Cc1ccc(C(F)(F)F)cc1] | 6 | | 90 | |
| 21a | 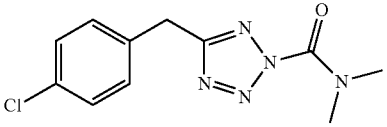 | 97 | | 93 | |
| 21b | 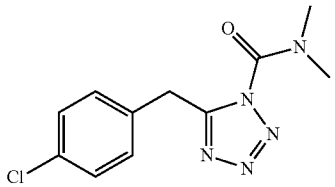 [SMILES: CN(C)C(=O)n1nnnc1Cc1ccc(Cl)cc1] | 54 | | 93 | |
| 22a | 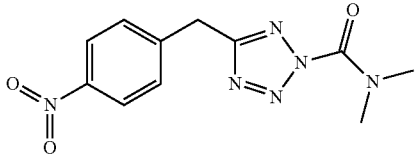 [SMILES: CN(C)C(=O)n1nnc(Cc2ccc([N+](=O)[O-])cc2)n1] | 97 | | 92 | |

TABLE 2-continued

| Number | Structure | % Inhibition of Enzyme by inhibitor at 10 nM and 1000 nM | | | |
| --- | --- | --- | --- | --- | --- |
| | | MGL | | FAAH | |
| | | 10 nM | 1000 nM | 10 nM | 1000 nM |
| 22b | | 22 | | 85 | |
| 23a | | 98 | | 91 | |
| 23b | | 60 | | 89 | |
| 24a | | 21 | | 47 | |
| 24b | | | 96 | | 100 |
| 25a | | | 99 | | 100 |
| 25b | | | 90 | | 88 |
| 26a | | 96 | | 93 | |

TABLE 2-continued

| Number | Structure | % Inhibition of Enzyme by inhibitor at 10 nM and 1000 nM | | | |
|---|---|---|---|---|---|
| | | MGL | | FAAH | |
| | | 10 nM | 1000 nM | 10 nM | 1000 nM |
| 26b | 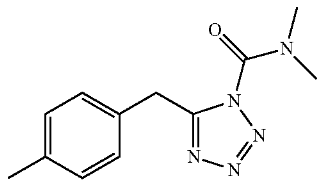 | 23 | | 85 | |
| 34 | 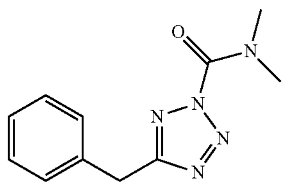 [SMILES: CN(C)C(=O)n1nnc(Cc2ccccc2)n1] | 100 | | 91 | |
| 35 | 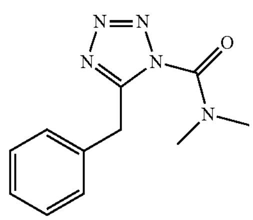 [SMILES: CN(C)C(=O)n1nnnc1Cc1ccccc1] | 41 | | 81 | |
| 36a | 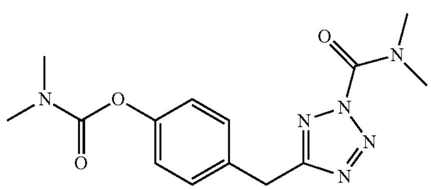 | 92 | | 80 | |
| 36b | 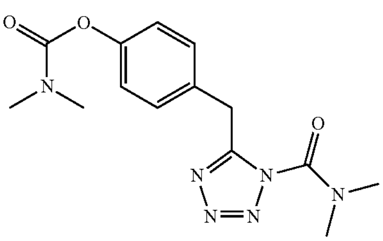 [SMILES: CN(C)C(=O)Oc1ccc(Cc2nnnn2C(=O)N(C)C)cc1] | 98 | | 82 | |
| 37 | 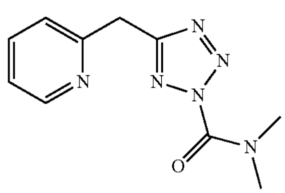 [SMILES: CN(C)C(=O)n1nnc(Cc2ccccn2)n1] | | | | |
| 38a | 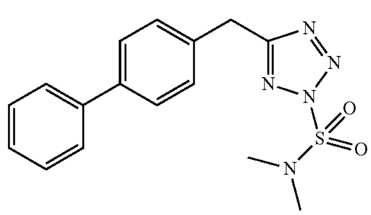 [SMILES: CN(C)S(=O)(=O)n1nnc(Cc2ccc(-c3ccccc3)cc2)n1] | | | 25 | |

TABLE 2-continued

| | | % Inhibition of Enzyme by inhibitor at 10 nM and 1000 nM | | | |
|---|---|---|---|---|---|
| | | MGL | | FAAH | |
| Number | Structure | 10 nM | 1000 nM | 10 nM | 1000 nM |
| 38b | | | | | |
| 39 | | | | 40 | 21 |
| 43 | | | | | 34 |
| 44 | | | | 10 | 12 |
| 45 | | 93 | | | |
| 46 | | 2 | 92 | | |

TABLE 2-continued

| | | % Inhibition of Enzyme by inhibitor at 10 nM and 1000 nM | | | |
| --- | --- | --- | --- | --- | --- |
| | | MGL | | FAAH | |
| Number | Structure | 10 nM | 1000 nM | 10 nM | 1000 nM |
| 50 | | | 42 (100 uM) | | 85 (100 uM) |
| 51 | | | 26 (100 uM) | | 30 |
| 54 | | | | | |
| 55 | | | | | |
| 56 | | | | | |
| 57 | | | | | |

TABLE 2-continued

| | | % Inhibition of Enzyme by inhibitor at 10 nM and 1000 nM | | | |
| | | MGL | | FAAH | |
| Number | Structure | 10 nM | 1000 nM | 10 nM | 1000 nM |
| --- | --- | --- | --- | --- | --- |
| 65 | 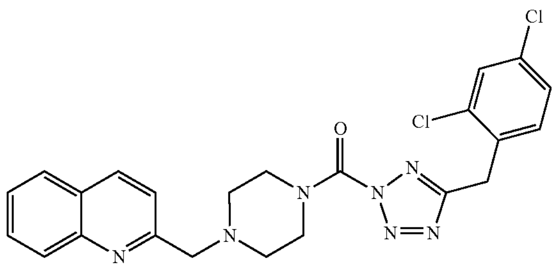 [SMILES: O=C(N1CCN(Cc2ccc3ccccc3n2)CC1)n1nnc(Cc2ccc(Cl)cc2Cl)n1] | | | 68 (100 uM) | |

*Mixture of isomers

TABLE 3

| | | % Inhibition of Enzyme by inhibitor at 10 nM and 1000 nM | | | |
| | | MGL | | FAAH | |
| Number | Structure | 10 nM | 1000 nM | 10 nM | 1000 nM |
| --- | --- | --- | --- | --- | --- |
| 28 | 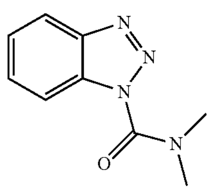 | | 30 | | 67 |
| 29 | 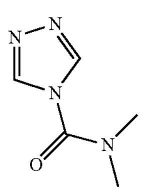 | | 79 | | 92 |
| 30 | 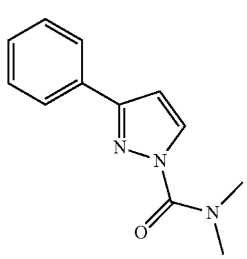 [SMILES: CN(C)C(=O)n1ccc(-c2ccccc2)n1] | | 11 | | 23 |
| 31 | 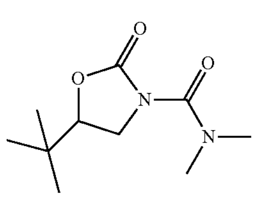 | | 66 | | 63 |

TABLE 3-continued

| | | % Inhibition of Enzyme by inhibitor at 10 nM and 1000 nM | | | |
| | | MGL | | FAAH | |
| Number | Structure | 10 nM | 1000 nM | 10 nM | 1000 nM |
|---|---|---|---|---|---|
| 32 | | | | 3 | 5 |
| 33 | | | | 6 | 88 |
| 47 | | | | 15 | 12  90  IC$_{50}$ = 78 nM |
| 48 | | | | 14 | 8  90 |
| 49 | | | | 7 | 25  90  IC$_{50}$ = 42 nM |

TABLE 3-continued

| | | % Inhibition of Enzyme by inhibitor at 10 nM and 1000 nM | | | |
| --- | --- | --- | --- | --- | --- |
| | | MGL | | FAAH | |
| Number | Structure | 10 nM | 1000 nM | 10 nM | 1000 nM |
| 52 | (3-phenyl-1,2,4-triazol-1-yl)-N,N-dimethylcarboxamide | 2 | 87 | | |
| 53 | 3-phenyl-1,2,4-triazole with N-(3-chloropropyl)-N-methylcarboxamide | 13 | 71 | | 100 |
| 59 | 2-benzyloxy-purine-7-N,N-dimethylcarboxamide | 86 (100 uM) | | 10 (100 uM) | |
| 60 | purine-7-N,N-dimethylcarboxamide | | 86 | | 96 |
| 61 | purine-9-N,N-dimethylcarboxamide | | 87 | | 87 |
| 62 | bis-N,N-dimethylcarboxamide oxo-purine derivative | | 83 | | 99 |
| 64 | 2-(quinolin-2-ylmethyl)piperazine with 4-phenylimidazole-1-carbonyl | 19 (100 uM) | | | |

TABLE 3-continued

| | | % Inhibition of Enzyme by inhibitor at 10 nM and 1000 nM | | | |
| | | MGL | | FAAH | |
| Number | Structure | 10 nM | 1000 nM | 10 nM | 1000 nM |
| --- | --- | --- | --- | --- | --- |
| 70 | [benzyl-triazole with N,N-dimethylcarboxamide; Mixture of isomers] | | 99 | | 98 |

*Mixture of isomers

TABLE 4

| Number | Structure | MGL $K_i$ | FAAH $K_i$ |
| --- | --- | --- | --- |
| 40 | [triazole sulfonamide] | 0.1 nM – 100 μM | 0.1 nM – 100 μM |
| 41 | [phenyl-imidazole sulfonamide] | 0.1 nM – 100 μM | 0.1 nM – 100 μM |
| 42 | [benzotriazole sulfonamide] | 0.1 nM – 100 μM | 0.1 nM – 100 μM |
| 58 | [triazolopyridine carboxamide] | 0.1 nM – 100 μM | 0.1 nM – 100 μM |
| 67 | [benzotriazole carboxamide] | 0.1 nM – 100 μM | 0.1 nM – 100 μM |
| 68 | [imidazopyridine carboxamide] | 0.1 nM – 100 μM | 0.1 nM – 100 μM |
| 69 | [imidazopyridine carboxamide isomer] | 0.1 nM – 100 μM | 0.1 nM – 100 μM |
| 71 | [imidazole carboxamide] | 0.1 nM – 100 μM | 0.1 nM – 100 μM |
| 72 | [bromo-imidazole carboxamide; Mixture of isomers] | 0.1 nM – 100 μM | 0.1 nM – 100 μM |

Figure 1B:
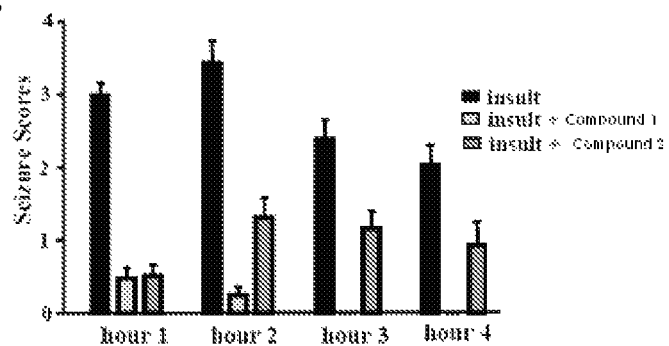
FIG. 1B is a graphic representation of seizure protection 1-4 hours after administration of compound 1 or 2.

These compounds were tested in vivo. Seizures were initiated in rats by injection with 10 mg/kg of KA (insult). Following administration of KA, animals were injected immediately with Vehicle, Compound 1 (5 mg/kg; n=6 or Compound 2 (5 mg/kg; n=6). Vehicle (control) treated rats did not receive KA or drug. FIGS. 1A and 1B show seizures were monitored and scored by blinded raters for 4 h following injections. Representative test results for isomeric compounds (1=2.5 disubstituted tetrazole and 2=1.5 disubstituted tetrazole) are given in FIGS. 1A and 1B. Compound 1 and Compound 2 reduce KA-induced seizure severity throughout the 4-h rating period.

Figure 2:
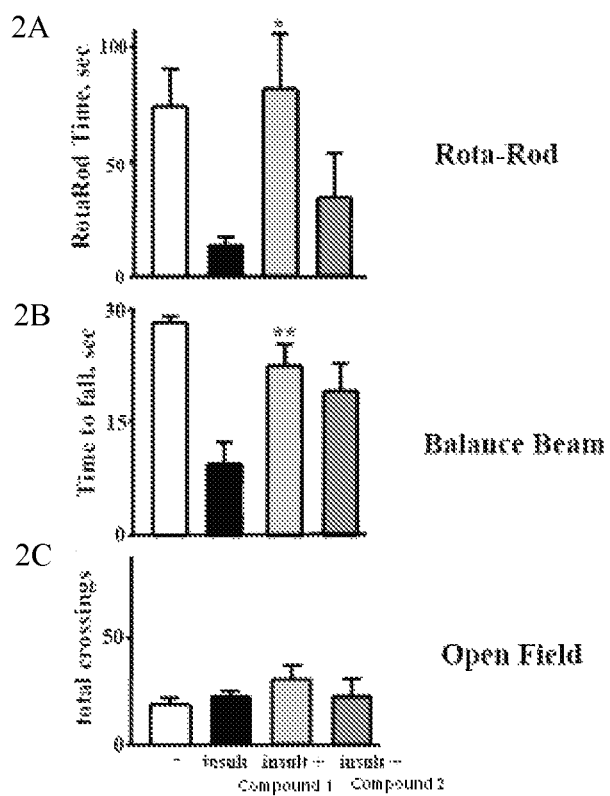
FIG. 2A is a graphic representation showing how animal coordination (rota-rod) is affected after administration of compound 1 or 2 immediately following KA administration.
FIG. 2B is a graphic representation showing how animal coordination (balance beam) is affected after administration of compound 1 or 2 immediately following KA administration.
FIG. 2C is a graphic representation showing how animal coordination (open field) is affected after administration of compound 1 or 2 immediately following KA administration.

FIGS. 2A-2C are graphic representations showing that animals received either vehicle, Compound 1, or Compound 2 (5 mg/kg) immediately following KA administration. At 24 h to 48 h post-injection, the animals were evaluated for alterations in movement. FIG. 2A: A rota-rod paradigm was used to assess coordination 24 h post-injection. Animals exposed to the excitotoxin alone had a marked impairment in coordination as determined by time on the rotating-rod (10 rpm). The insult-exposed animals that were immediately treated with Compound 1 had improved rota-rod performance compared to the excitotoxin alone (ANOVA: P<0.0001; POST-HOC test compared with insult only data: *p<0.05).

FIG. 2B: The KA insult disrupted balance as presented by mean time to fall (sec)±SEM off the elevated beam. Treatment with Compound 1 protected against the excitotoxic-induced behavioral impairment (ANOVA: p<0.0002: post-hoc test compared with insult only data: **p<0.01).

FIG. 2C: The rats were monitored for locomotor activity in a novel open field. The distance of exploration was unchanged across treatment groups as measured by total number of segments crossed.

6. Synthesis of Compounds of Formula (I)

Certain inhibitory compounds were prepared according to the following schemes and methods.

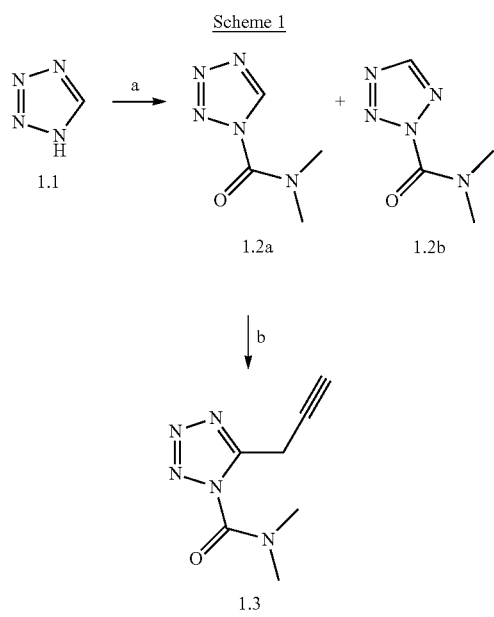

(a) dimethylcarbamoyl chloride, Et$_3$N, CH$_3$CN, r.t., 3 h; (b)NaH, DMF, propargyl bromide, r.t., 2 d

A. N,N-dimethyl-2H-tetrazole-2-carboxamide (1a/1.2a) and N,N-dimethyl-1H-tetrazole-2-carboxamide (1b/1.2b)

Et$_3$N (5.3 mmol, 0.75 mL) followed by dimethylcarbamoyl chloride (4.6 mmol, 0.43 mL) were added slowly into the precooled (0-5 C) solution of tetrazole (1.1) in acetonitrile (3.54 mmol, 0.45 M). Reaction was warmed to RT and stirring was continued for 3 h. Acetonitrile was evaporated under vacuum using Rotavapor and the residue was dissolved in ethylacetate. The solution was washed two times with saturated NaHCO$_3$ (aq) and aqueous layer was extracted with ethyl acetate. Combined organic layers were dried on MgSO$_4$ and evaporated under vacuum on Rotavapor. The crude residue thus obtained was purified by flash chromatography using Biotage SP1 eluting with 0-5% of ethyl acetate in dichloromethane. Two isomers were successfully separated by flash chromatography on SiO2 using Biotage SP1 by eluting with 0-10% ethylacetate in dichloromethane (1a:1b; 10:1, overall yield 75%).

The compounds were confirmed as follows: $^1$H NMR (CDCl$_3$) for 1a: δ 3.26 (s, 3H), 3.38 (s, 3H), 9.18 (s, 1H). $^1$H NMR (CDCl$_3$) for 1b: 3.10 (s, 3H), 3.29 (s, 3H), 8.66 (s, 1H).

B. N,N-dimethyl-5-prop-2-yn-1-yl-1H-tetrazole-1-carboxamide (2/1.3)

1.2a (2.9 mmol, 410 mg) in dry DMF (1 mL) was added into precooled (0-5° C.) solution of NaH (4.2 mmol, 100 mg, 60% in mineral oil) in dry DMF (1 mL). The cooling bath was removed and stirring was continued for 45 min at RT. Propargyl bromide (3.0 mmol, 0.27 mL) was added slowly and stirring was continued for 2 days at 50° C. The solution was cooled, quenched with water and extracted several times with ethyl acetate. The combined organic layers were dried on MgSO$_4$ and evaporated under vacuum on Rotavapor and the crude product was purified by flash chromatography using Biotage SP1 by eluting with 0-5% ethyl acetate in dichloromethane.

The compound was confirmed as follows: $^1$H NMR (CDCl$_3$): δ 2.49 (s, 1H), 3.08 (s, 6H), 4.26 (d, 1H, $^2$J=2.5 Hz).

Scheme 2

Compounds 3-10, 12-13, 16-27, 34-37, 39, 45, 46, 50-52, 56, 57 and 66-69 were made by Scheme 2 and the following methods.

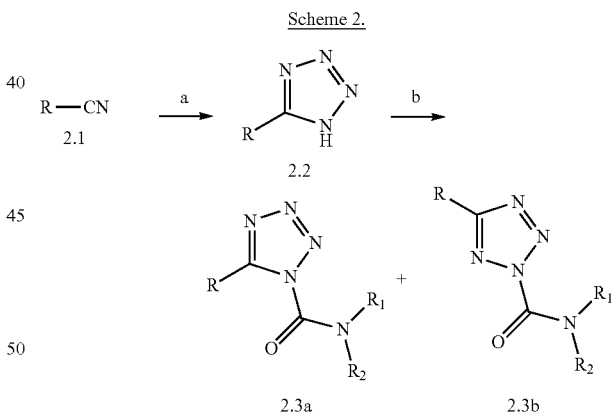

(a) NaN$_3$, ZnBr$_2$, i-PrOH/H$_2$O, MW, 160° C., 15 min; (b) R$_1$R$_2$NCOCl, Et$_3$N, CH$_3$CN, r.t., 12 h.

A. General Method 2A

A mixture of corresponding nitrile (2.1, 1 mmol), NaN$_3$ (2 mmol) and ZnBr$_2$ (0.5 mmol) in i-PrOH:H$_2$O (1:2, 4 mL) was heated in a microwave at 160° C. for 15 min. 2M HCl and ethyl acetate were added and the mixture was stirred until all the solids were dissolved in organic layer. Solution was passed through SPE column containing hydromatrix HMN, ethyl acetate fractions were collected and evaporated under vacuum on Rotavapor. The residue was taken in acetonitrile and an excess of corresponding carbamoyl chloride and Et$_3$N were added. The mixture was stirred at RT temperature overnight. Acetonitrile was evaporated and the crude product was purified by flash chromatography on Biotage SP1 eluting with 0-5% ethyl acetate in dichloromethane. The regioisomers (2.3a and 2.3b) were well separated in most of the cases.

1. 5-(1H-indol-2-yl)-N,N-dimethyl-1H-tetrazole-1-carboxamide (3a)

Compound 3a was confirmed as follows: $^1$H NMR (CDCl$_3$): δ 3.23 (s, 3H), 3.30 (s, 3H), 7.27-7.34 (m, 2H), 7.46-7.48 (m, 1H), 8.10 (d, 1H, $^3J$=2.8 Hz), 8.36-8.38 (m, 1H), 8.57 (s, 1H).

2. 5-(1H-indol-2-yl)-N,N-dimethyl-2H-tetrazole-1-carboxamide (3b)

Compound 3b was confirmed as follows: $^1$H NMR (CDCl$_3$): δ 3.10 (s, 6H), 7.34-7.44 (m, 2H), 7.26 (d, 1H, $^3J$=8.2 Hz), 7.76 (d, 1H, $^3J$=7.7 Hz), 7.82 (s, 1H).

3. N,N-dimethyl-5-(2-oxo-2-phenylethyl)-1H-tetrazole-1-carboxamide (4)

Compound 4 was confirmed as follows: $^1$H NMR (CDCl$_3$): δ 3.10 (s, 3H), 3.25 (s, 3H), 4.69 (s, 2H), 7.50 (t, 2H, $^3J$=7.5 Hz), 7.61 (t, 1H, $^3J$=7.4 Hz), 8.03 (d, 2H, $^3J$=7.2 Hz).

4. N,N-dimethyl-5-(pyridin-3-yl-methyl)-1H-tetrazole-1-carboxamide (5)

Compound 5 was confirmed as follows: $^1$H NMR (CDCl$_3$): δ 3.10 (s, 3H), 3.26 (s, 3H), 4.35 (s, 2H), 7.28 (t, 1H, $^3J$=3.9 Hz), 7.71 (d, 1H, $^3J$=7.9 Hz), 8.53 (d, 1H, $^3J$=3.9 Hz), 8.63 (s, 1H).

5. 4-{[5-(2,4-dichlorobenzyl)-tetrazol-2-yl]carbonyl}morpholine (6)

Compound 6 was confirmed as follows: $^1$H NMR (CDCl$_3$): δ 3.44 (t, 1H, $^3J$=4.5 Hz), 3.57 (s, 1H), 3.63 (t, 1H, $^3J$=4.5 Hz), 3.73-3.77 (m, 3H), 3.85 (br s, 2H), 4.42 (s, 1H), 4.52 (s, 1H), 7.23-7.31 (m, 2H), 7.42 (s, 1H).

6. 5-(2,4-dichlorobenzyl)-N-methyl-N-phenyl-2H-tetrazole-2-carboxamide (7a)

Compound 7a was confirmed as follows: $^1$H NMR (CDCl$_3$): δ 3.58 (s, 3H), 4.21 (s, 2H), 6.90 (br s, 1H), 7.04 (br s, 2H), 7.13 (dd, 1H, $^3J$=8.2 Hz $^2J$=1.9 Hz), 7.23 (br s, 3H), 7.35 (d, 1H, $^3J$=2.1 Hz).

7. 5-(2,4-dichlorobenzyl)-N-methyl-N-phenyl-1H-tetrazole-2-carboxamide (7b)

Compound 7b was confirmed as follows: $^1$H NMR (CDCl$_3$): δ 3.51 (s, 3H), 4.52 (s, 2H), 6.88 (br s, 2H), 7.24-7.28 (m, 5H), 7.47 (d, 1H, $^3J$=1.5 Hz).

8. 5-(2,4-dichlorobenzyl)-N,N-diphenyl-2H-tetrazole-2-carboxamide (8a)

Compound 8a was confirmed as follows: $^1$H NMR (CDCl$_3$): δ 4.24 (s, 2H), 6.91 (d, 1H, $^3J$=8.2 Hz), 7.14 (dd, 1H, $^3J$=8.3 Hz, $^2J$=2.2 Hz), 7.19-7.33 (m, 10H), 7.36 (d, 1H, $^3J$=2.2 Hz).

9. 5-(2,4-dichlorobenzyl)-N,N-diphenyl-1H-tetrazole-2-carboxamide (8b)

Compound 8b was confirmed as follows: $^1$H NMR (CDCl$_3$): δ 4.56 (s, 2H), 7.08 (br s, 3H), 7.27-7.33 (m, 9H), 7.49 (br s, 1H).

10. 5-(2,4-dichlorobenzyl)-N,N-diethyl-tetrazole-2-carboxamide (9)

Compound 9 was confirmed as follows: $^1$H NMR (CDCl$_3$): δ 1.19-1.26 (m, 4H), 1.34 (t, 2H, $^3J$=7.0 Hz), 3.20 (qv, 1H, $^3J$=7.1 Hz), 3.29 (qv, 1H, $^3J$=6.9 Hz), 3.50 (qv, 1H, $^3J$=7.1 Hz), 3.60 (qv, 1H, $^3J$=6.9 Hz), 4.42 (s, 1H), 4.52 (s, 1H), 7.22-7.25 (m, 1H), 7.28-7.31 (m, 1H), 7.40-7.42 (m, 1H).

11. 5-(2,4-dichlorobenzyl)-N,N-diisopropyl-tetrazole-2-carboxamide (10)

Compound 10 was confirmed as follows: $^1$H NMR (CDCl$_3$): δ 1.10-1.61 (m, 12H), 3.56-3.67 (m, 2H), 4.41 (s, 1H), 4.51 (s, 1H), 7.22-7.27 (m, 1H), 7.30-7.33 (m, 1H), 7.39-7.47 (m, 1H).

12. 1-{[5-(2,4-dichlorobenzyl)-tetrazol-1-yl]carbonyl}piperidine, mixture of isomers (12)

Mixture of compound 12 isomers was confirmed as follows: $^1$H NMR (CDCl$_3$): δ 1.67-1.77 (m, 6H), 3.24-3.28 (m, 1H), 3.35-3.36 (m, 1H), 3.64 (br s, 1H), 3.75-3.77 (m, 1H), 4.42 (qv, 1H, $^3J$=4.4 Hz), 4.50 (qv, 1H, $^3J$=4.5 Hz), 7.21-7.32 (m, 2H), 7.40-7.43 (m, 1H). m/z 340.26.

13. 5-(2,4-dichlorobenzyl)-1-(pyrrolidin-1-ylcarbonyl)-tetrazole, mixture of isomers (13)

Mixture of compound 13 isomers was confirmed as follows: $^1$H NMR (CDCl$_3$): δ 1.93-2.05 (m, 4H), 3.61-3.67 (m, 1H), 3.73-3.78 (m, 1H), 4.42 (qv, 1H, $^3J$=4.4 Hz), 4.56 (qv, 1H, $^3J$=4.5 Hz), 7.20-7.30 (m, 2H), 7.40-7.43 (m, 1H). m/z 326.25.

14. 5-(4-bromobenzyl)-N,N-dimethyl-2H-tetrazole-2-carboxamide (16a)

Compound 16a was confirmed as follows: $^1$H NMR (CDCl$_3$): δ 3.11 (s, 3H), 3.27 (s, 3H), 4.29 (s, 2H), 7.24 (d, 2H, $^3J$=8 Hz), 7.45 (d, 2H, $^3J$=8 Hz).

15. 5-(4-bromobenzyl)-N,N-dimethyl-1H-tetrazole-2-carboxamide (16b)

Compound 16b was confirmed as follows: $^1$H NMR (CDCl$_3$): δ 2.83 (s, 3H), 3.12 (s, 3H), 4.42 (s, 2H), 7.16 (d, 2H, $^3J$=8 Hz), 7.45 (d, 2H, $^3J$=8 Hz).

16. 5-(2,4-dichlorobenzyl)-N,N-dimethyl-2H-tetrazole-2-carboxamide (17a)

Compound 17a was confirmed as follows: $^1$H NMR (CDCl$_3$): δ 3.08 (s, 3H), 3.25 (s, 3H), 4.43 (s, 2H), 7.22-7.24 (m, 1H), 7.29 (d, 1H, $^3J$=8.3 Hz), 7.42 (d, 1H, $^3J$=2.1 Hz).

17. 5-(2,4-dichlorobenzyl)-N,N-dimethyl-1H-tetrazole-2-carboxamide (17b)

Compound 17b was confirmed as follows: $^1$H NMR (CDCl$_3$): δ 2.30 (s, 3H), 3.16 (s, 3H), 4.50 (s, 2H), 7.25-7.26 (m, 1H), 7.29 (d, 1H, $^3$J=8.3 Hz), 7.42 (d, 1H, $^3$J=2.0 Hz).

18. 5-(4-iodobenzyl)-N,N-dimethyl-2H-tetrazole-2-carboxamide (18a)

Compound 18a was confirmed as follows. $^1$H NMR (CDCl$_3$): δ 3.10 (s, 3H), 3.26 (s, 3H), 4.26 (s, 2H), 7.10 (d, 2H, $^3$J=8.4 Hz), 7.65 (d, 2H, $^3$J=8.4 Hz).

19. 5-(4-iodobenzyl)-N,N-dimethyl-1H-tetrazole-2-carboxamide (18b)

Compound 18b was confirmed as follows: $^1$H NMR (CDCl$_3$): δ 2.82 (s, 3H), 3.11 (s, 3H), 4.39 (s, 2H), 7.02 (d, 2H, $^3$J=8.3 Hz), 7.65 (d, 2H, $^3$J=8.3 Hz).

20. N,N-dimethyl-5-[4-(trifluoromethyl)benzyl]-2H-tetrazole-2-carboxamide (20a)

Compound 20a was confirmed as follows: $^1$H NMR (CDCl$_3$): δ 3.12 (s, 3H), 3.28 (s, 3H), 4.41 (s, 2H), 7.49 (d, 2H, $^3$J=8.1 Hz), 7.60 (d, 2H, $^3$J=8.2 Hz).

21. N,N-dimethyl-5-[4-(trifluoromethyl)benzyl]-1H-tetrazole-2-carboxamide (20b)

Compound 20b was confirmed as follows: $^1$H NMR (CDCl$_3$): δ 2.87 (s, 3H), 3.11 (s, 3H), 4.52 (s, 2H), 7.42 (d, 2H, $^3$J=8.1 Hz), 7.59 (d, 2H, $^3$J=8.2 Hz).

22. N,N-dimethyl-5-(4-nitrobenzyl)-2H-tetrazole-2-carboxamide (22a)

Compound 22a was confirmed as follows: $^1$H NMR (CDCl$_3$): δ 3.11 (s, 3H), 3.27 (s, 3H), 4.44 (s, 2H), 7.53 (d, 2H, $^3$J=8.5 Hz), 8.20 (d, 2H, $^3$J=8.7 Hz).

23. N,N-dimethyl-5-(4-nitrobenzyl)-1H-tetrazole-2-carboxamide (22b)

Compound 22b was confirmed as follows: $^1$H NMR (CDCl$_3$): δ 3.02 (s, 3H), 3.17 (s, 3H), 4.57 (s, 2H), 7.49 (d, 2H, $^3$J=8.7 Hz), 8.19 (d, 2H, $^3$J=8.7 Hz).

24. 5-(4-methoxybenzyl)-N,N-dimethyl-2H-tetrazole-2-carboxamide (24a)

Compound 24a was confirmed as follows: $^1$H NMR (CDCl$_3$): δ 3.10 (s, 3H), 3.25 (s, 3H), 3.78 (s, 3H), 4.26 (s, 2H), 6.85 (d, 2H, $^3$J=8.7 Hz), 7.27 (d, 2H, $^3$J=8.6 Hz).

25. 5-(4-methoxybenzyl)-N,N-dimethyl-1H-tetrazole-2-carboxamide (24b)

Compound 24b was confirmed as follows: $^1$H NMR (CDCl$_3$): δ 2.66 (s, 3H), 3.07 (s, 3H), 3.78 (s, 3H), 4.38 (s, 2H), 6.84 (d, 2H, $^3$J=8.7 Hz), 7.17 (d, 2H, $^3$J=8.7 Hz).

26. N,N-dimethyl-5-(4-methylbenzyl)-2H-tetrazole-2-carboxamide (26a)

Compound 26a was confirmed as follows: $^1$H NMR (CDCl$_3$): δ 2.32 (s, 3H), 3.09 (s, 3H), 3.24 (s, 3H), 4.28 (s, 2H), 7.12 (d, 2H, $^3$J=7.8 Hz), 7.23 (d, 2H, $^3$J=7.9 Hz).

27. N,N-dimethyl-5-(4-methylbenzyl)-1H-tetrazole-2-carboxamide (26b)

Compound 26b was confirmed as follows: $^1$H NMR (CDCl$_3$): δ 2.32 (s, 3H), 2.64 (s, 3H), 3.06 (s, 3H), 4.40 (s, 2H), 7.10-7.14 (m, 4H).

28. 5-(biphenyl-4-ylmethyl)-N,N-dimethyl-2H-tetrazole-2-carboxamide (27a)

Compound 27a was confirmed as follows: $^1$H NMR (CDCl$_3$): δ 3.11 (s, 3H), 3.26 (s, 3H), 4.37 (s, 2H), 7.32-7.57 (m, 9H).

29. 5-(biphenyl-4-ylmethyl)-N,N-dimethyl-1H-tetrazole-1-carboxamide (27b)

Compound 27b was confirmed as follows: $^1$H NMR (CDCl$_3$): δ 2.70 (s, 3H), 3.07 (s, 3H), 4.48 (s, 2H), 7.32-7.56 (m, 9H).

30. 5-benzyl-N,N-dimethyl-2H-tetrazole-2-carboxamide (34)

Compound 34 was confirmed as follows: $^1$H NMR (CDCl$_3$): δ 3.12 (s, 3H), 3.27 (s, 3H), 4.35 (s, 2H), 7.26-7.38 (m, 5H).

31. 5-benzyl-N,N-dimethyl-1H-tetrazole-1-carboxamide (35)

Compound 35 was confirmed as follows: $^1$H NMR (CDCl$_3$): δ 2.76 (s, 3H), 3.09 (s, 3H), 4.46 (s, 2H), 7.26-7.38 (m, 5H).

32. 4((2-(dimethylcarbamoyl)-2H-tetrazol-5-yl)methyl)phenyl dimethylcarbamate (36a)

Compound 36a was confirmed as follows: $^1$H NMR (CDCl$_3$): δ 3.01 (s, 3H), 3.10 (s, 3H), 3.11 (s, 3H), 3.26 (s, 3H), 4.32 (s, 2H), 7.06 (d, J=8 Hz, 2H), 7.34 (d, J=8 Hz, 2H).

33. 4-((1-(dimethylcarbamoyl)-1H-tetrazol-5-yl)methyl)phenyl dimethylcarbamate (36b)

34. N,N-dimethyl-5-(pyridin-2-ylmethyl)-2H-tetrazole-2-carboxamide (37)

Compound 37 was confirmed as follows: $^1$H NMR (CDCl$_3$): δ 3.08 (s, 6H), 4.22 (s, 2H), 7.20 (dd, J=5, 7 Hz, 1H), 7.28 (d, J=10 Hz, 1H), 7.65 (td, J=7, 2 Hz, 1H), 8.05 (d, J=7 Hz, 1H).

35. N,N-dimethyl-5-(pyridin-4-ylmethyl)-2H-tetrazole-2-carboxamide (39)

Compound 39 was confirmed as follows: $^1$H NMR (CDCl$_3$): δ 3.04 (s, 6H), 4.06 (s, 2H), 7.23 (d, J=6 Hz, 2H), 8.56 (d, J=6 Hz, 2H).

36. 5-(2-chlorobenzyl)-N,N-dimethyl-2H-tetrazole-2-carboxamide (45)

Compound 45 was confirmed as follows: $^1$H NMR (CDCl$_3$): δ 3.09 (s, 3H), 3.26 (s, 3H), 4.48 (s, 2H), 7.27-7.42 (m, 4H).

37. 5-(difluoro(phenyl)methyl)-N,N-dimethyl-2H-tetrazole-2-carboxamide (46)

Compound 46 was confirmed as follows: $^1$H NMR (CDCl$_3$): δ 3.25 (s, 6H), 7.51 (t, J=7 Hz, 2H), 7.64 (t, J=7 Hz, 1H), 8.48 (d, J=7 Hz, 2H).

38. N,N-dimethyl-5-(naphthalen-1-ylmethyl)-2H-tetrazole-2-carboxamide (50)

Compound 50 was confirmed as follows: $^1$H NMR (CDCl$_3$): δ 3.05 (s, 6H), 4.25 (s, 2H), 7.28-7.85 (m, 7H).

39. N,N-dimethyl-3-phenyl-1H-1,2,4-triazole-1-carboxamide (52)

Compound 52 was confirmed as follows: $^1$H NMR (CDCl$_3$): δ 3.20 (bh, 6H), 7.44 (m, 3H), 8.15 (m, 2H), 8.84 (s, 1H).

40. 5-(biphenyl-2-ylmethyl)-N,N-dimethyl-2H-tetrazole-2-carboxamide (56)

Compound 56 was confirmed as follows: $^1$H NMR (CDCl$_3$): δ 3.06 (s, 3H), 3.25 (s, 3H), 4.32 (s, 2H), 7.28-7.44 (m, 9H).

41. 5-(biphenyl-2-ylmethyl)-N,N-dimethyl-1H-tetrazole-1-carboxamide (57)

Compound 57 was confirmed as follows: $^1$H NMR (CDCl$_3$): δ 2.82 (s, 3H), 3.06 (s, 3H), 4.42 (s, 2H), 7.26-7.42 (m, 9H).

42. 5-(4-fluorobenzyl)-N,N-dimethyl-2H-tetrazole-2-carboxamide (66a)

Compound 66a was confirmed as follows: $^1$H NMR (CDCl$_3$): δ 3.10 (s, 3H), 3.25 (s, 3H), 4.29 (s, 2H), 6.98-7.03 (m, 2H), 7.30-7.33 (m, 2H).

43. 5-(4-fluorobenzyl)-N,N-dimethyl-1H-tetrazole-1-carboxamide (66b)

Compound 66b was confirmed as follows: $^1$H NMR (CDCl$_3$): δ 2.76 (s, 3H), 3.09 (s, 3H), 4.41 (s, 2H), 6.99-7.02 (m, 2H), 7.23-7.26 (m, 2H).

Scheme 3

Compounds 11, 28, 29-33, 38, 40-42, 52 and 59-62 were synthesized by the following scheme and methods:

Scheme 3

A. General Method 3A

Compound 3.1 (N-excessive NH-heterocyclic compound, 1 mmol) was dissolved in acetonitrile (20 mL) and cooled to 0-5° C. and was added triethylamine (5 mmol) followed by appropriate carbamyl chloride/sulfamoyl chloride 3.2 (3 mmol). The reaction was warmed to r.t. and stirred for 12 h. Reaction was quenched by adding aqueous NaHCO$_3$ (10 mL) and extracted with dichloromethane (3×50 mL). Organic layers were pooled, dried on MgSO4 and solvent was evaporated under vacuum on Rotavapor to give a residue which was purified by flash chromatography on SiO2 using Biotage SP1 using acetone/hexane as gradient eluent (0% acetone to 60% acetone over 12 column volumes). Pure fractions identified by UV were collected and solvent was evaporated on Rotavapor to give a homogenous compound (3.3) consistent with the structure assigned based on $^1$H NMR and MS analysis.

B. General Method 3B

Compound 3.1 (1 mmol), triethylamine (5 mmol) and appropriate carbamoy/sulfamoyl chloride 3.2 (3 mmol) were taken in acetonitrile (4 mL) and placed in a 10 mL microwave reactor vial. The reaction mixture was microwaved at 120° C. for 10 min using Biotage Initiator or CEM Discover single mode microwave synthesizer. Workup and purification was done as described in Method B to give compounds represented by formula 3.3.

C. General Method 3C

Compound 3.1 (1 mmol) in dichloromethane (30 mL) was cooled on an ice-bath and phosgene (20% in toluene, 2 mmol) was added. Ice bath was removed and reaction was brought to r.t. and stirred for 4 h. Reaction was cooled to 0-5° C. and appropriate amine (1.2 mmol) followed by triethylamine (6 mmol) were added. Reaction was warmed to RT and stirred for 8-12 h. Workup and purification was done as described in method B to obtain compounds represented by formula 3.4.

1. N-(4-chlorobutyl)-5-(2,4-dichlorobenzyl)-N-methyl-1H-tetrazole-1-carboxamide (11)

Compound 11 was confirmed as follows: $^1$H NMR (CDCl$_3$): δ 1.16-1.67 (m, 1H), 1.78-1.91 (m, 3H), 1.58 (s, 2H), 3.23 (s, 1H), 3.30 (t, 1H, $^3J$=7.7 Hz), 3.47 (t, 1H, $^3J$=6.2 Hz), 3.59-3.65 (m, 2H), 4.43 (s, 2H), 7.23-7.32 (m, 2H), 7.42 (d, 1H, $^2J$=2.0 Hz). m/z 376.30.

2. N,N-dimethyl-1H-benzo[d][1,2,3]-triazole-1-carboxamide (28)

Compound 28 was confirmed as follows: $^1$H NMR (CDCl$_3$): δ 3.30 (bs, 6H), 7.43 (t, J=7 Hz, 1H), 7.58 (t, J=7 Hz, 1H), 8.0 (d, J=9 Hz, 1H), 8.19 (d, J=9 Hz, 1H).

3. N,N-dimethyl-4H-1,2,4-triazole-4-carboxamide (29)

Compound 29 was confirmed as follows: $^1$H NMR (CDCl$_3$): δ 3.22 (bs, 6H), 8.0 (s, 1H), 8.8 (s, 1H).

4. N,N-dimethyl-3-phenyl-1H-pyrazole-1-carboxamide (30)

Compound 30 was confirmed as follows: $^1$H NMR (CDCl$_3$): δ 3.33 (bs, 6H), 6.7 (d, J=3 Hz, 1H), 7.37 (m, 1H), 7.43 (m, 2H), 7.86 (m, 2H), 8.19 (d, J=3 Hz, 1H).

5. 5-tert-butyl-N,N-dimethyl-2-oxooxazolidine-3-carboxamide (31)

Compound 31 was confirmed as follows: $^1$H NMR (CDCl$_3$): δ 0.93 (s, 9H), 2.05 (m, 1H), 3.06 (s, 3H), 3.17 (s, 3H), 4.22 (dd, J=9, 6 Hz, 1H), 4.41 (dd, J=9, 5 Hz).

6. 5-benzyl-N,N-dimethyl-2-oxooxazolidine-3-carboxamide (32)

Compound 32 was confirmed as follows: $^1$H NMR (CDCl$_3$): δ 2.79 (dd, J=13, 8 Hz, 1H), 3.03 (s, 6H), 3.18 (dd, J=13, 4 Hz, 1H), 4.07 (t, J=10 Hz, 1H), 4.29 (t, J=8 Hz, 1H), 4.75 (m, 1H), 7.16 (d, J=7 Hz, 2H), 7.26-7.35 (m, 3H).

7. N,N-dimethyl-4-phenyl-1H-imidazole-1-carboxamide (33)

Compound 33 was confirmed as follows: $^1$H NMR (CDCl$_3$): δ 3.18 (s, 6H) 7.30 (t, J=7 Hz, 1H), 7.41 (t, J=8 Hz, 2H), 7.54 (d, J=2 Hz, 1H), 7.81 (d, J=8 Hz, 2H), 7.96 (d, J=2 Hz, 1H).

8. 5-(biphenyl-4-ylmethyl)-N,N-dimethyl-1H-tetrazole-1-sulfonamide (38b)

Compound 38b was confirmed as follows: $^1$H NMR (CDCl$_3$): δ 3.05 (s, 6H), 4.55 (s, 2H), 7.35 (t, J=7 Hz, 1H), 7.41-7.59 (m, 8H).

9. N,N-dimethyl-4H-1,2,4-triazole-4-sulfonamide (40)

Compound 40 was confirmed as follows: $^1$H NMR (CDCl$_3$): δ 3.02 (s, 6H), 8.01 (s, 1H), 8.61 (s, 1H).

10. N,N-dimethyl-4-phenyl-1H-imidazole-1-sulfonamide (41)

Compound 41 was confirmed as follows: $^1$H NMR (CDCl$_3$): δ 2.92 (s, 6H), 7.33 (t, J=7 Hz, 1H), 7.42 (t, J=7 Hz, 2H), 7.52 (d, J=2 Hz, 1H), 7.80 (m, 2H), 7.96 (d, J=2 Hz, 1H).

11. N,N-dimethyl-1H-benzo[d][1,2,3]-triazole-1-sulfonamide (42)

Compound 42 was confirmed as follows: $^1$H NMR (CDCl$_3$): δ 3.11 (s, 6H), 7.49 (m, 1H), 7.64 (t, J=7 Hz, 1H), 8.0 (d, J=2 Hz, 1H), 8.14 (d, J=7 Hz, 1H).

12. N,N-dimethyl-3-phenyl-1H-1,2,4-triazole-1-carboxamide (52)

Compound 52 was confirmed as follows: $^1$H NMR (CDCl$_3$): δ 3.20 (bh, 6H), 7.44 (m, 3H), 8.15 (m, 2H), 8.84 (s, 1H).

13. 2-(benzyloxy)-N,N-dimethyl-7H-purine-7-carboxamide (59)

Compound 59 was confirmed as follows: $^1$H NMR (CDCl$_3$): δ 3.18 (bs, 6H), 5.71 (s, 2H), 7.33-7.41 (m, 3H), 7.55 (d, J=10 Hz, 2H), 8.26 (s, 1H), 8.62 (s, 1H).

14. N,N-dimethyl-7H-purine-7-carboxamide (60)

Compound 60 was confirmed as follows: $^1$H NMR (CDCl$_3$): δ 3.24 (s, 6H), 8.56 (s, 1H), 9.18 (s, 1H), 9.23 (s, 1H).

15. N,N-dimethyl-9H-purine-9-carboxamide (61)

Compound 61 was confirmed as follows: $^1$H NMR (CDCl$_3$): δ 3.20 (s, 6H), 8.46 (s, 1H), 9.07 (s, 1H), 9.22 (s, 1H).

16. $N^1,N^1,N^9,N^9$-tetramethyl-6-oxo-5,6-dihydro-4H-purine-1,9-dicarboxamide (62)

Compound 62 was confirmed as follows: $^1$H NMR (CDCl$_3$): δ 2.81 (s, 3H), 3.12 (s, 6H), 3.22 (s, 3H), 8.40 (s, 1H), 8.81 (s, 1H).

Scheme 4

Compounds 47-49 and 53 were made by the following scheme and methods:

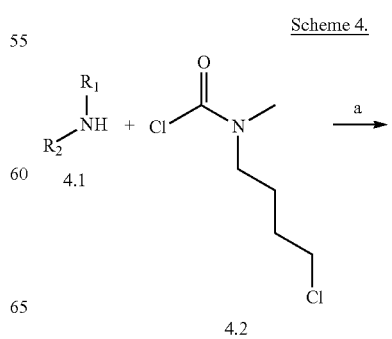

-continued

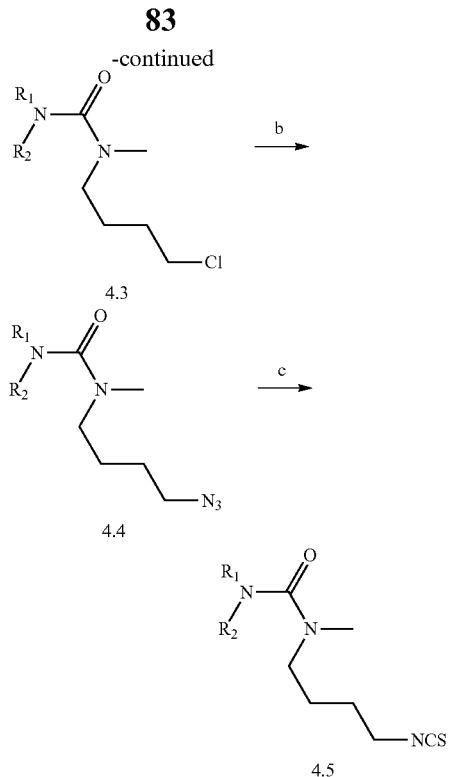

(a) NEt₃, CH₃CN, 0° C. to r.t., 12 h; (b) Bu₄NN₃, acetone, reflux, 8 h; (c) PPh₃, toluene, 50° C., 2 h; CS₂, 50° C., 2 h.

1. N-(4-chlorobutyl)-N-methyl-4-phenyl-1H-imidazole-1-carboxamide (47)

Compound 47 was confirmed as follows: 4-phenyl-1H-imidazole (4.1) and N-(4-chlorobutyl)-N-methylcarbamoyl chloride (4.2) were treated as described in method B to obtain N-(4-chlorobutyl)-N-methyl-4-phenyl-1H-imidazole-1-carboxamide (47). ¹H NMR (CDCl₃): δ 1.84-1.93 (m, 4H), 3.17 (s, 3H), 3.53 (t, J=7 Hz, 2H), 3.60 (t, J=7 Hz, 2H), 7.30 (t, J=8 Hz, 1H), 7.41 (t, J=8 Hz, 2H), 7.52 (d, J=2 Hz, 1H), 7.81 (d, J=8 Hz, 2H), 7.95 (d, J=2 Hz, 1H).

2. N-(4-azidobutyl)-N-methyl-4-phenyl-1H-imidazole-1-carboxamide (48)

Compound 47 (4.3) (1 mmol) was taken in anhydrous acetone (25 mL) and tetra-n-butylammonium azide (2 mmol) was added and the reaction was refluxed for 8 h. The reaction was cooled to RT and solvent was evaporated on Rotavapor to give a crude compound which on purification by Biotage SP1 provided pure N-(4-azidobutyl)-N-methyl-4-phenyl-1H-imidazole-1-carboxamide (48/4.4).

Compound 48 was confirmed as follows: ¹H NMR (CDCl₃): δ 1.64-1.83 (m, 4H), 3.16 (s, 3H), 3.37 (t, J=7 Hz, 2H), 3.51 (t, J=7 Hz, 2H), 7.30 (t, J=8 Hz, 1H), 7.41 (t, J=8 Hz, 2H), 7.52 (d, J=2 Hz, 1H), 7.81 (d, J=8 Hz, 2H), 7.95 (d, J=2 Hz, 1H).

3. N-(4-isothiocyanatobutyl)-N-methyl-4-phenyl-1H-imidazole-1-carboxamide (4.5/49)

To a compound 48 (0.85 mmol) in anhydrous toluene (20 mL) was added triphenylphosphine (1 mmol) and reaction mixture was stirred at 50° C. for 2 h. Carbondisulfide (10 mmol) was added and the stirring continued at 50° C. for 4 h. Reaction was cooled to r.t. and solvent was evaporated on Rotavapor to give a crude compound which on purification by Biotage SP1 gave a pure isothiocyante 49.

Compound 49 was confirmed as follows: ¹H NMR (CDCl₃): δ 1.72-1.91 (m, 4H), 3.19 (s, 3H), 3.52 (t, J=7 Hz, 2H), 3.60 (t, J=7 Hz, 2H), 7.29 (t, J=8 Hz, 1H), 7.39 (t, J=8 Hz, 2H), 7.53 (d, J=2 Hz, 1H), 7.81 (d, J=8 Hz, 2H), 7.95 (d, J=2 Hz, 1H).

4. N-(4-chlorobutyl)-N-methyl-3-phenyl-1H-1,2,4-triazole-1-carboxamide (53)

Compound 53 was confirmed as follows: ¹H NMR (CDCl₃): δ 1.71-1.85 (m, 4H), 2.81 (s, 3H), 3.55 (t, J=6 Hz, 2H), 3.62 (t, J=6 Hz, 2H), 7.44 (m, 3H), 8.14 (m, 2H), 8.85 (s, 1H).

Scheme 5

Compounds 43 and 44 were made by the following scheme and procedure:

Scheme 5

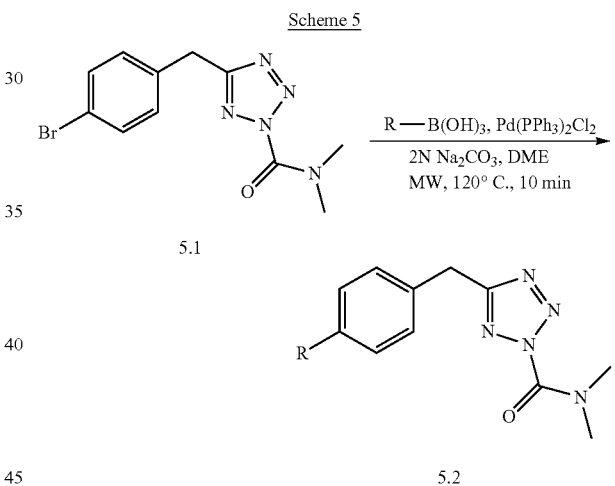

A. General Method 5

Compound 5.1 (1 mmol), appropriate boronic acid (2 mmol), 2 M Na₂CO₃ (3 mmol) and Pd(PPh₃)₂Cl₂ (0.3 mmol) were taken in DME/H2O/EtOH (7:3:2, 4 mL) and the mixture was placed in a 10 mL microwave reactor tube. The reaction was microwaved using Biotage Initiator or CEM Discover microwave synthesizer for 5 min at 140° C. Solvent was evaporated and crude residue was purified on SiO₂ using Biotage SP1 to give a pure product which on NMR and MS analysis showed consistence with the assigned structure represented by formula 5.2.

1. N,N-dimethyl-5-(4-(pyridin-3-yl)benzyl)-2H-tetrazole-2-carboxamide (43)

Compound 43 was confirmed as follows: ¹H NMR (CDCl₃): δ 3.06 (s, 6H), 4.13 (s, 2H), 7.37 (dd, J=8, 5 Hz, 1H), 7.43 (d, J=5 Hz, 2H), 7.56 (d, J=5 Hz, 2H), 7.87 (dt, J=8, 2 Hz, 1H), 8.61 (dd, J=5, 2 Hz, 1H), 8.85 (d, J=2 Hz, 1H).

2. N,N-dimethyl-5-(4-(pyridin-4-yl)benzyl)-2H-tetrazole-2-carboxamide (44)

Compound 44 was confirmed as follows: $^1$H NMR (CDCl$_3$): δ 3.05 (s, 6H), 4.12 (s, 2H), 7.43 (d, J=8 Hz, 2H), 7.51 (d, J=6 Hz, 2H), 7.62 (d, J=8 Hz, 2H), 8.67 (bs, 2H).

Scheme 6

Compounds 64 and 65 were made by the below scheme and procedure:

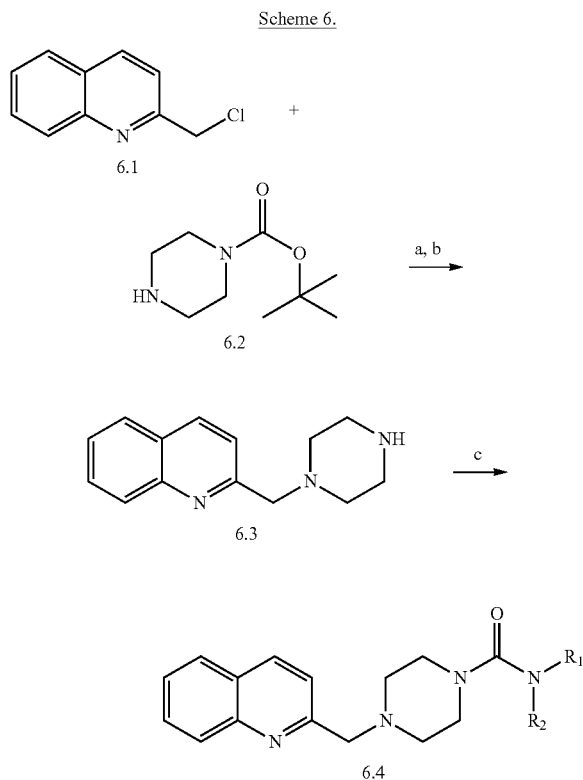

(a) K$_2$CO$_3$, acetone, reflux, 12 h; (b) CF$_3$COOH, CH$_2$Cl$_2$, 0° C. to r.t., 2 h; (c) 1M COCl$_2$, CH$_2$Cl$_2$, 0° C. to r.t., 4 h; R$_1$R$_2$NH, NEt$_3$, r.t., 6 h

1. Intermediate 2-(piperazin-1-ylmethyl)quinoline (6.3)

To a solution of 2-chloromethylquinoline hydrochloride (5 mmol) in anhydrous acetone (100 mL) was added, anhydrous potassium carbonate (15 mmol) and tert-butyl piperazine-1-carboxylate (7 mmol) and the reaction mixture was stirred under reflux conditions for 12 h. Reaction was cooled to r.t. and filtered through celite. Filtrate was concentrated on Rotavapor under vacuum and the crude residue was purified on SiO$_2$ using Biotage SP1 to give a pure 2-(piperazin-1-ylmethyl)quinoline (6.3, 92%, pale yellow solid).

Intermediate Compound 6.3 was confirmed as follows: $^1$H NMR (CDCl$_3$): δ 2.54 (bs, 4H), 2.93 (t, J=5 Hz, 4H), 3.84 (s, 2H), 7.51 (t, J=7 Hz, 1H), 7.66 (d, J=9 Hz, 1H), 7.69 (t, J=7 Hz, 1H), 7.81 (d, J=8 Hz, 1H), 8.08 (d, J=9 Hz, 1H), 8.13 (d, J=9 Hz, 1H).

A. General Method 6A

Compound 6.3 in dichloromethane (1 mmol) was cooled on ice-bath and phosgene (20% in toluene, 2 mmol) was added and the reaction mixture was allowed to warm to RT The reaction was continued stirring at RT for 4 h and then cooled again on ice-bat. Appropriate NH-heterocyclic compound (2 mmol) followed by triethylamine (4 mmol) were added and the reaction was warmed to RT. Reaction was stirred at RT for 6 h, diluted with dicholormethane and washed with aq NaHCO$_3$. Organic layer was dried on MgSO$_4$ and solvent was evaporated on Rotavapor under vacuum. The crude residue thus obtained was purified on SiO$_2$ using Biotage SP1 to give pure compound represented by formula 6.4.

1. (4-phenyl-1H-imidazol-1-yl)(4-(quinolin-2-ylmethyl)piperazin-1-yl)methanone (64)

Compound 64 was confirmed as follows: $^1$H NMR (CDCl$_3$): δ 2.69 (t, J=5 Hz, 4H), 3.72 (t, J=5 Hz, 4H), 3.94 (s, 2H), 7.29 (t, J=7 Hz, 1H), 7.40 (t, J=7 Hz, 2H), 7.48 (d, J=2 Hz, 1H), 7.55 (t, J=7 Hz, 1H), 7.61 (d, J=7 Hz, 1H), 7.72 (t, J=7 Hz, 1H), 7.80 (d, J=10 Hz, 2H), 7.83 (d, J=7 Hz, 1H), 7.93 (d, J=2 Hz, 1H), 8.09 (d, J=7 Hz, 1H), 8.17 (d, J=7 Hz, 1H).

2. (5-(2,4-dichlorobenzyl)-2H-tetrazol-2-yl)(4-(quinolin-2-ylmethyl)piperazin-1-yl)methanone (65)

Compound 65 was confirmed as follows: $^1$H NMR (CDCl$_3$): δ 2.62 (m, 4H), 3.68-3.81 (m, 4H), 3.90 (s, 2H), 7.26-7.33 (m, 1H), 7.54 (t, J=7 Hz, 2H), 7.60 (d, J=7 Hz, 1H), 7.72 (t, J=7 Hz, 1H), 7.83 (d, J=7 Hz, 1H), 8.09 (d, J=7 Hz, 1H), 8.16 (d, J=7 Hz, 1H).

3. N,N-dimethyl-1H-benzimidazole-1-carboxamide (67)

Compound 67 was confirmed as follows: $^1$H NMR (CDCl$_3$): δ 3.11 (s, 6H), 7.30-7.37 (m, 2H), 7.55 (d, 1H, $^3$J=7.8 Hz), 7.78 (d, 1H, $^3$J=7.8 Hz), 8.16 (s, 1H). m/z 190.

4. N,N-dimethyl-3H-imidazo[4,5-b]pyridine-3-carboxamide (68)

Compound 68 was confirmed as follows: $^1$H NMR (CDCl$_3$): δ 3.19 (s, 6H), 7.34 (dd, 1H, $^2$J=4.8 Hz, $^3$J=8.1 Hz), 8.00 (dd, 1H, $^2$J=1.5 Hz, $^3$J=8.1 Hz), 8.4 (s, 1H), 8.63 (dd, 1H, $^2$J=1.6 Hz, $^3$J=4.8 Hz). m/z 191.

Scheme 7

Compound 70 was made by the following scheme and experimental procedure:

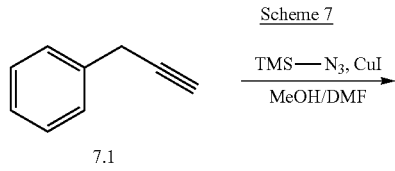

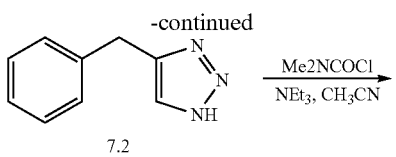

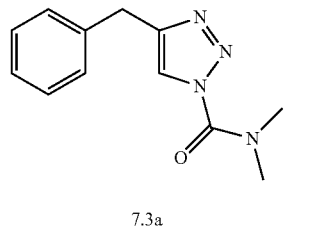

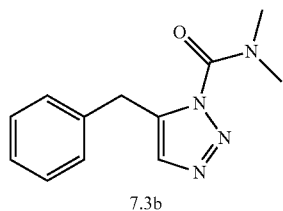

1.
4-benzyl-N,N-dimethyl-1,2,3-triazole-1-carboxamide (70)

To a solution of compound 7.1 (1 mmol) in DMF/MeOH (10:1, 20 mL), was added CuI (0.5 mmol) and TMS-N$_3$ (1 mmol) and the reaction mixture was heated to 100° C. and stirred at this temperature for 2 days. The reaction was cooled to RT and passed through Fluorosil and eluted with EtOAc (100 mL). The organic layers were collected and solvent was evaporated on Rotavapor under vacuum. Crude compound was purified on SiO$_2$ using Biotage SP1 flash chromatography system to give a pure 4-benzyl-N,N-dimethyl-1,2,3-triazole-1-carboxamide (70).

Compound 70 was confirmed as follows: $^1$H NMR (CDCl$_3$): δ 3.20 (s, 3H), 3.36 (s, 3H), 4.13 (s, 2H), 7.25-7.35 (m, 5H), 7.80 (s, 1H).

Synthesis of (5Z,8Z,11Z,14Z)-6-methoxy-4-methyl-2-oxo-2H-chromen-7-yl icosa-5,8,11,14-tetraenoate An exemplary fluorogenic substrate (shown) was made as described below.

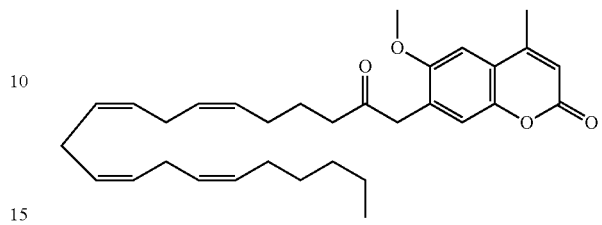

To a stirred solution of 7-hydroxy-6-methoxy-4-methyl-2H-chromen-2-one (2.0 g, 9.7 mmoles) in anhydrous DMF were added 1-ethyl-3-(3'-dimethylaminopropyl)carbodiimide (5.5 g, 29.1 mmoles), 4-Dimethylaminopyridine (3.6 g, 29.1 mmoles), and arachidonic acid (2.9 g, 9.5 mmoles). The reaction mixture was stirred for 24 h. The reaction mixture was then extracted with ethyl acetate, washed with hydrochloric acid, water and brine. The organic layer was dried over sodium sulfate and evaporated and the crude product was purified by flash chromatography (40% acetone/hexanes) to provide the title compound as a colorless oil (4.0 g, 83%).

The compound was confirmed as follows: $^1$H NMR (500 MHz, CDCl$_3$-d) 7.40 (s, 1H), 7.07 (s, 1H), 6.39 (s, 1H), 5.22-5.63 (m, 8H), 3.82 (s, 3H), 2.56-2.73 (m, 6H), 2.41 (s, 3H) 2.40 (t, J=7.2 Hz, 2H), 2.21-2.31 (m, 4H), 1.81-1.96 (m, 2H), 1.67-1.80 (m, 6H), 0.88 (t, J=6.4 Hz, 3H).

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:
1. A compound having the formula:

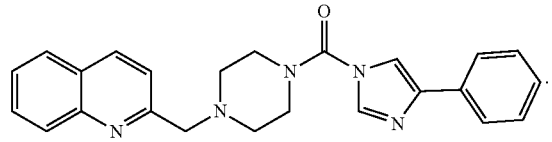 [SMILES: O=C(N1CCN(Cc2ccc3ccccc3n2)CC1)n1cnc(-c2ccccc2)c1]

* * * * *